US006806257B1

(12) United States Patent
Lee et al.

(10) Patent No.: US 6,806,257 B1
(45) Date of Patent: Oct. 19, 2004

(54) FLAVONES AS INDUCIBLE NITRIC OXIDE SYNTHASE INHIBITORS, CYCLOOXYGENASE-2 INHIBITORS AND POTASSIUM CHANNEL ACTIVATORS

(75) Inventors: Tony Jer-Fu Lee, Springfield, IL (US); Chen Ling Ling Yang, Taipei (TW)

(73) Assignee: Board of Trustees of Southern Illinois University, Springfield, IL (US)

(*) Notice: Subject to any disclaimer, the term of this patent is extended or adjusted under 35 U.S.C. 154(b) by 399 days.

(21) Appl. No.: 09/693,130

(22) Filed: Oct. 20, 2000

Related U.S. Application Data
(60) Provisional application No. 60/160,612, filed on Oct. 20, 1999.

(51) Int. Cl.$^7$ ............................................... A61K 31/70
(52) U.S. Cl. ......................... 514/23; 514/25; 514/456; 514/453; 514/465
(58) Field of Search ............................. 514/456, 465, 514/453, 25, 23, 680, 27

(56) References Cited

U.S. PATENT DOCUMENTS

| | | | |
|---|---|---|---|
| 5,013,852 A | 5/1991 | Walenta et al. | |
| 5,071,872 A | 12/1991 | Witiak et al. | |
| 5,447,719 A | 9/1995 | Kamataki | |
| 5,612,310 A | 3/1997 | Dewhirst et al. | |
| 5,849,733 A | 12/1998 | Kim | |
| 5,889,003 A | 3/1999 | Dhainaut et al. | |
| 6,048,850 A | 4/2000 | Young et al. | |
| 6,184,246 B1 * | 2/2001 | Manthey et al. | 514/456 |
| 6,194,469 B1 * | 2/2001 | Nair et al. | 514/886 |
| 6,262,073 B1 * | 7/2001 | Hopper et al. | 514/312 |
| 6,294,526 B1 * | 9/2001 | Higuchi et al. | 514/192 |

OTHER PUBLICATIONS

Marletta, M. et al., "Macrophage Oxidation of L–Arginine to Nitrite and Nitrate: Nitric Oxide is an Intermediate," *Biochemistry*, (1988), 27:8706–811.
Fein, A., "Treatment of Severe Systemic Inflammatory Response Syndrome and Sepsis with a Novel Bradykinin Antagonist, Deltibant (CP–0127)," *J. Am. Med Assoc.*, (1977), vol. 277, pp. 482–487.
Palmer, R. et al., "Nitric Oxide Release Accounts for the Biological Activity of Endothelium–Derived Relaxing Factor," *Nature*, (1987), 327:524–526.
Palmer, R. et al., "Vascular Endothelial Cells Sythesize Nitric Oxide from L–Arginine," *Nature*, (1988), 333:664–666.
Moncada, S. et al., "Biosynthesis of Nitric Oxide From L–Arginine," *Biochemical Pharmacology*, (1989), 38:1709–1717.
Furchgott, R., "Studies on Endothelium–Dependent Vasolidation and the Endothelium–Derived Relaxing Factor," *Acta Physiol. Scand.*, (1990), 139:257–270.
Ignarro, L., "Biosynthesis and Metabolism of Endothelium–Derived Nitric Oxide," *Annu. Rev. Phamacol. Toxicol.*, (1990), 30:535–560.

Hibbs, J. et al., "Macrophage Cytotoxicity: Role for L–Arginine Deiminase and Imino Nitrogen Oxidation to Nitrite," *Science*, (1987), 235:473–476.
McCall, T. et al., "Synthesis of Nitric Oxide from L–Arginine by Neutrophils," *Biochem. J.*, (1989), 261:293–296.
Salvemini, D. et al., "Human Neutrophils and Mononuclear Cells Inhibit Platelet Aggregation by Releasing a Nitric Oxide–Like Factor," *Proc. Natl. Acad. Sci. USA*, (1989), 86:6328–6332.
Wright, C. et al. "Generation of Nitric Oxide by Human Neutrophils," *Biochemical and Biophysical Research Communications*, (1989), 160:813–819.
Amber, I. et al., "Cytokines Induce and L–Arginine–Dependent Effector System in Nonmacrophage Cells," *Journal of Leukocyte Biology*, (1988), 44:58–65.
Palacios, M. et al., "Nitric Oxide from L–Arginine Stimulates the Soluble Guanylate Cyclase in Adrenal Glands," *Biochemical Biophysical Research Communication*, (1989), 165:802–809.
Billiar, T. et al. "An L–Arginine–Dependent Mechanism Mediates Kupffer Cell Inhibition of Hepatocyte Protein Synthesis in Vitro," *J. Exp. Med.*, (1989), 169:1467–1472.
Garthwaite, J. et al., "Endothelium–Derived Relaxing Factor Release on Activation of NMDA Receptors Suggests Role as Intercellular Messenger in the Brain," *Nature*, (1989), 36:385–388.
Knowles, R. et al., "Formation of Nitric Oxide from L–Arginine in the Central Nervous System: A Transduction Mechanism for Stimulation of the Soluble Guanylate Cyclase," *Proc. Natl. Acad. Sci. USA*, (1989), 86:5159–5162.
Ignarro, L. et al., "Endothelium–Derived Relaxing Factor Produced and Released from Artery and Vein is Nitric Oxide," *Proc. Natl. Acad. Sci. USA*, (1987), 84:9265–9269.
Radomski, M. et al., "The Role of Nitric Oxide and cGMP in Platelet Adhesion to Vascular Endothelium," *Biochemical Biophysical Research Communications.*, (1987), 148:1482–1489.
Hibbs, J. et al., "L–Arginine is Required for Expression of the Activated Macrophage Effector Mechanism Causing Selective Metabolic Inhibition in Target Cells," *The Journal of Immunology*, (1987), vol. 138, 550–565, No. 2.

(List continued on next page.)

Primary Examiner—James H. Reamer
(74) Attorney, Agent, or Firm—Wood, Phillips, Katz, Clark & Mortimer

(57) ABSTRACT

The present invention is directed to a method for inhibiting expression of either iNOS or COX-2, or both in mammals using flavone compounds, and pharmaceutically acceptable salts thereof. The present invention is also directed to a method of activating K$^+$ channels in mammals; as well as methods for treating septic shock, for inhibiting expression of angiotensin converting enzyme, for treating or preventing aneurysms and for reducing inflammation and related pathological changes using these compounds. Presently preferred compounds are oroxylin A (5,7-dihydroxy-6-methoxy flavone) and wogonin (5,7-dihydroxy-8-methoxy flavone).

50 Claims, 27 Drawing Sheets

OTHER PUBLICATIONS

Bredt, D. et al., "Nitric Oxide Mediates Glutamate–Linked Enhancement of cGMP levels in the Cerebellum," *Proc. Natl. Acad. Sci. USA*, (1989), 86:9030–9033.

Iyengar, R. et al., "Macrophage Synthesis of Nitrite, Nitrate, and N–Nitrosamines: Precursors and Role of the Respiratory Bursts," *Proc. Natl. Acad. Sci. USA*, (1987), 84:6369–6373.

Bredt, D. et al., "Isolation of Nitric Oxide Sythetase, a Calmodulin–Requiring Enzyme," *Proc. Natl. Acad. Sci. USA*, (1990), 87:682–685.

Tayeh, M. et al., "Macrophage Oxidation of L–Arginine to Nitric Oxide, Nitrite, and Nitrate," *J. Biol. Chem.*, (1989), 264:19654–19658.

Soo Kwon, N. et al., "Reduced Biopterin as a Cofactor in the Generation of Nitrogen Oxides by Murine Macrophages," *The Journal of Biological Chemistry*, (1989), 264:20496–20501.

Knowles, R. et al., "Differential Induction of Brain, Lung and Liver Nitric Oxide Synthase by Endotoxin n the Rat," *Biochem J.*, (1990), 270:833–836.

Moore, P. et al., "L–$N^G$–Nitro Arginine (L–NOARG), a Novel, L–Arginine–Reversible Inhibitor of Endothelium–Dependent Vasodilation in Vitro," *Br. J. Pharmacol.*, (1990), 99:408–412.

Bult, H. et al., "Nitric Oxide as an Inhibitory Non–Adrenergic Non–Cholinergic Neurotransmitter," *Nature*, (1990), 345:346–347.

Gillespie, J. et al., "The Effects of L–Arginine and $N^G$–Monomethyl L–Arginine on the Response of the Rat Anococcygeus Muscle to NANC Nerve Stimulation," *Br. J. Pharmacol*, (1989), 98:1080–1082.

Ramagopal, M. et al., "Effects of $N^G$–Monomethyl–LArginine on Field Stimulation–Induced Decreases in Cytosolic $Ca^{2+}$ Levels and Relaxation in the Rat Anococcygeus Muscle," *Eur. J. Pharmacol.*, (1989), 174:297–299.

Ferrendelli, J. et al. "Elevation of Cyclic GMP Levels in Central Nervous System by Excitatory and Inhibitory Amino Acids," *Journal of Neurochemistry*, (1974), 22:535–540.

Choi, D., "Cerebral Hypoxia: Some New Approaches and Unanswered Questions," *The Journal of Neuroscience*, (1990), 10:2493–2501.

Meldrum, B. et al., "Excitatory Amino Acid Neurotoxicity and Neurodegenerative Disease," *Trends in Pharmacol. Sci.*, (1990), 11:379–387.

Duval, D. et al., "Characterization of Hepatic Nitric Oxide Sythase: Identification as the Cytokine–Inducible Form Primarily Regulated by Oxidants," *Molecular Pharmacology*, (1996), 50:277–84.

Yuan, T., "Characterization of the $Ca^{2+}$–Dependent and – Independent Interactions between Calmodulin and its Binding Domain of Inducible Nitric Oxide Synthase," *Febs. Lett.*, (1998), 431:210–4.

Pedoto, A. et al., "Treatment of Septic Shock in Rats with Nitric Oxide Synthase Inhibitors and Inhaled Nitric Oxide," *Crit. Care Med.*, (1998), 26:2021–8.

Quan, N. et al., "Cyclooxygenase 2 mRNA Expression in Rat Brain after Peripheral Injection of Lipopolysaccharide," *Brain Res.*, (1998), 802:189–197.

Lee, S.H. et al., "Selective Expression of Mitogen–Inducible Cyclooxygenase in Macrophages Stimulated with Lipopolysaccharide," *J. Biol. Chem.*, (1992), 267:25934–25938.

Naylor, A. et al., "Oroxylin," *J. Chem Soc.*, (1901), 79:954–956.

Varady, J., "Ring Isomerization of Flavones, New Synthesis of Oroxylin–A and 7–Methyl–Oroxylin–A," *Tetrahedron Letters*, (1965), No. 48, pp. 4281–4282.

Kim, H. et al., "Chloromethyl Ketones Block Induction of Nitric Oxide Synthase in Murine Macrophages by Preventing Activation of Nuclear Factor–kappa B," *J. Immunol.*, (1995), 153:4741–4748.

Muller, J. et al., "Nuclear Factor kappa B, a Mediator of Lipopolysaccharide Effects," *Immunobiology*, (1993), 187, 233–256.

Chen, Y.C. et al., "Involvement of Reactive Oxygen Species and Caspase 3 Activation in Arsenite–Inducted Apoptosis," *Journal of Cellular Physiology*, (1998), 177:324–333.

Cao, C. et al., "Induction by Lipopolysaccharide of Cyclooxygenase–2 mRNA in Rat Brain; its Possible Role in the Febril Response," *Brain Research* 697, (1995), 187–196.

Kim, Y.M., "Upstream NF–kappa B Site is Required for the Maximal Expression of Mouse Inducible Nitric Oxide Synthase Gene in Interferon–Gamma Plus Lipopolysaccharide–Induced RAW 264.7 Macrophages," *Biochemical and Biophysical Research Communications*, (1997), 236, 655–660.

Faraci, Frank M. et al., "Role of Potassium Channels in Regulation of Cerebral Vascular Tone" *Journal of Cerebral Blood Flow and Metabolism*, 18:1047–1063, 1998.

Nelson, Mark T., et al., "Physiological Roles and Properties of Potassium Channels in Arterial Smooth Muscle," *Am. J. Physiol* C:799–C822, 1995.

Fukuda, Shunichi et al., "Prevention of Rat Cerebral Aneurysm Formation by Inhibition of Nitric Oxide Synthase," *Circulation*, 101 (21) pp. 2532–2538, (2000).

Miralles, Manuel, et al., "Indomethacin Inhibits Expansion of Experimental Aortic Aneurysms via Inhibition of the cox2 Isoform of Cyclooxygenase," *Journal of Vascular Surgery*, vol. 29 No. 5, pp. 884–893, 1999.

Sreerama, V. V. et al., "Nuclear Oxidation in Flavones and Related Compounds," *Proc. Indian Acad. Sci.* 29A, pp. 1–8, 1949.

Shah, R. C. et al., "The Constitution of Oroxylin–A, a Yellow Colouring Matter from the Root–bark of Oroxylum Indicum," *J. Chem. Soc.*, 131:591–593, 1936.

Database HCAPLUS on STN, Hecker et al. 'Inhibition by antioxidants of nitric oxide synthase expression in murine macrophages: role of nuclear factor .kappa B and interferon regulatory factor 1'. Br. J. Pharmacol., 118(8), 2178–2184 (1996).

Database HCAPLUS on STN, AN 1996:532781, Hoult et al. 'Inhibition of leukocyte 5–lipoxygenase and cyclo–oxygenase but not constitutive nitric oxide synthase by tanetin, a novel flavonol derived from feverfew, Tanacetum parthenium', Pharm. Sci. 1(2), 71–74 (1995).

Database HCAPLUS on STN, AN 1994:261034, Vaccari et al. Potent, extra–channel influence of several calcium–channel modulators on striatal binding of [3H]tyramine. Neurochem. Res., 18(11), 1125–30 (1993).

Database HCAPLUS on STN, AN 1994:499294. Eugui et al. 'Some antioxidants inhibit, in a coordinate fashion, the production of tumor necrosis factor–alpha, IL–beta by human peripheral blood mononuclear cells'. Int. Immun., 6(3), 409–22 (1994).

Database HCAPLUS on STN, AN 1999:453550. Wang et al. 'Quantitative structure–activity relationship analysis of the inhibitory effect on flavonoids on angiotensin converting enzyme'. Chin. Pharm. J. (Taipei), 51(2), 149–162 (1999).

Database HCAPLUS on STN, AN 1999:96114. Murphy et al. 'Method and composition using 12–hydroperoxyeicosatetraenoic acid (12–HPETE) and analogs for protection from damage by ischemia', WO 9904783 (Feb. 16, 1999).

* cited by examiner

MYRICITRIN (N1)

OROXYLIN A (N2)

PENTA-O-GALLOYL-β-GLUCOPYRANOSE (N3)

WOODFORDIN C (N4)

OENOTHEIN B (N5)

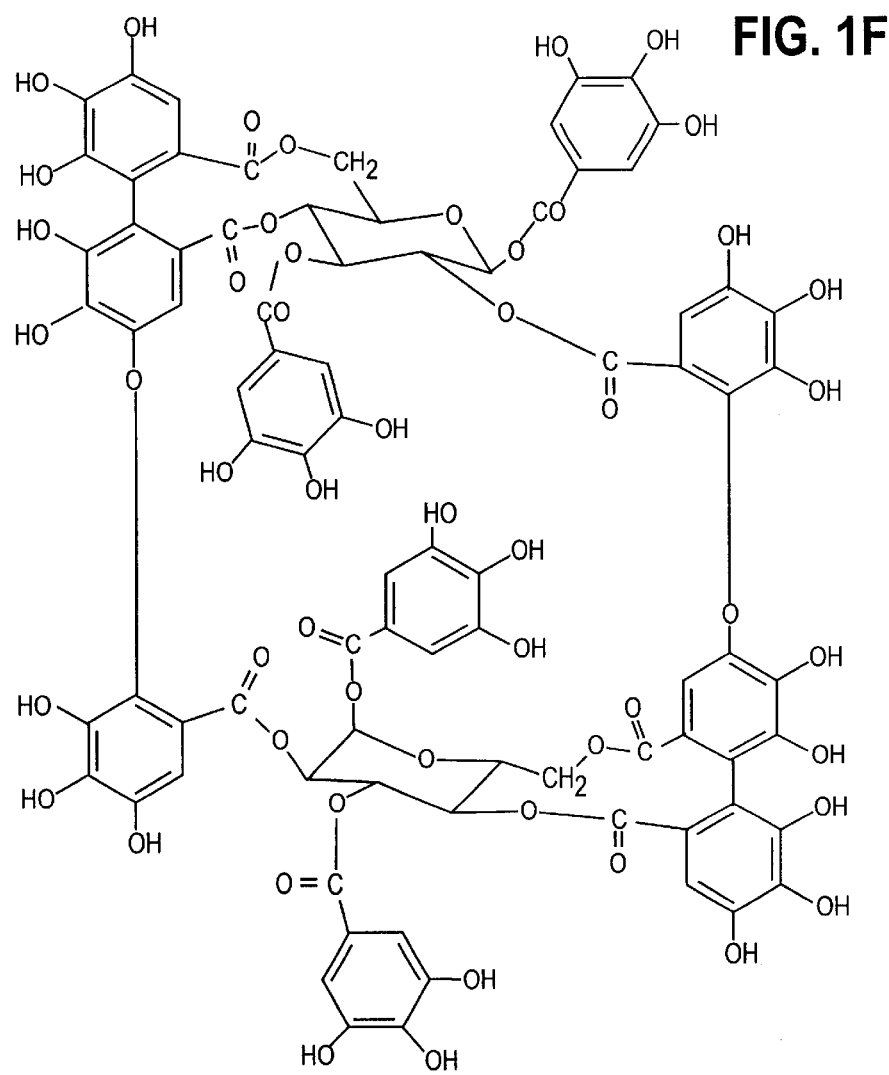
CUPHIIN D1 (N6)
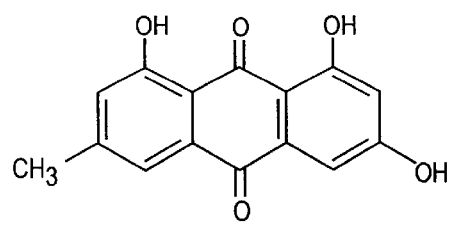
EMODIN (N7)
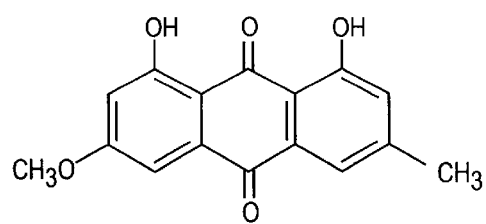
PHYSCION (N8)
FIG. 1F
FIG. 1G
FIG. 1H

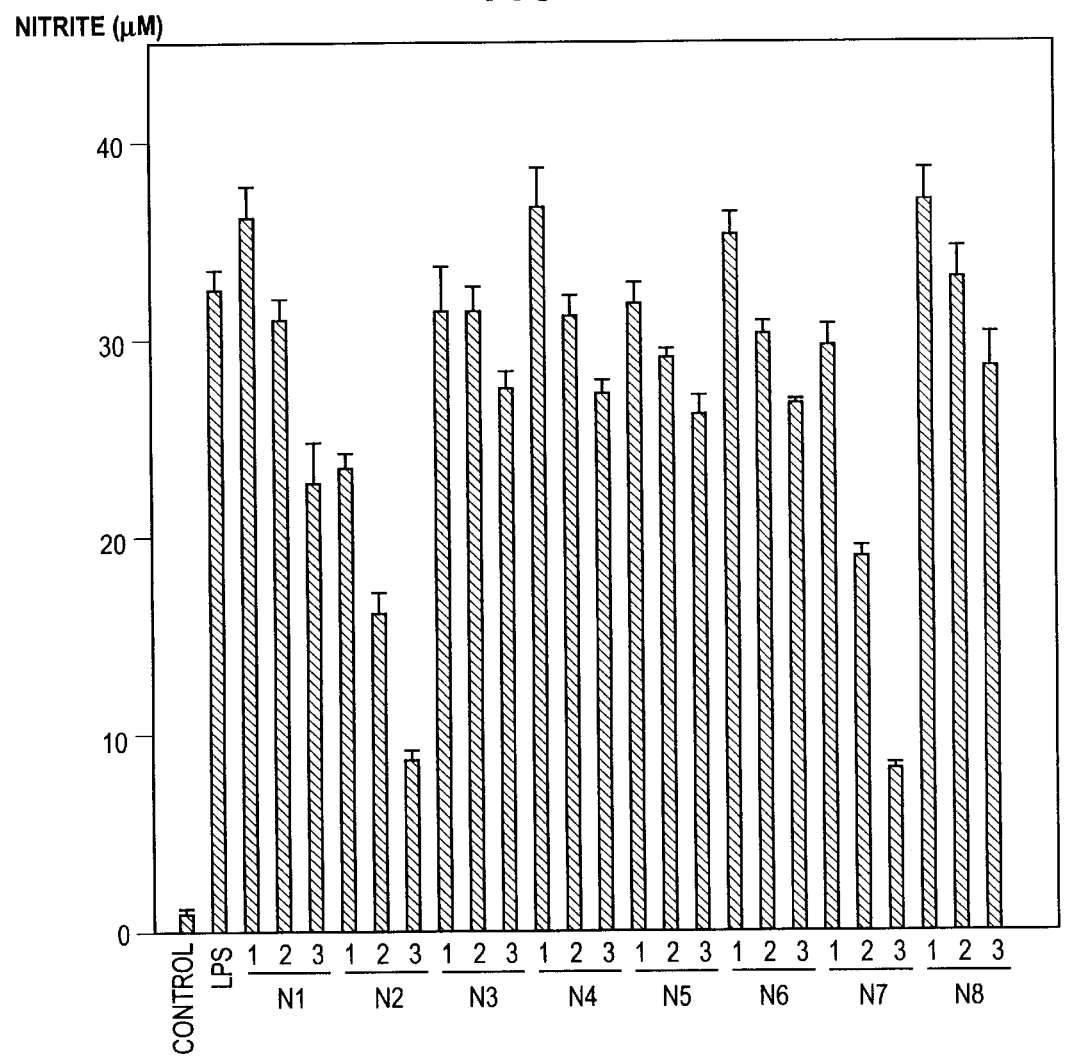

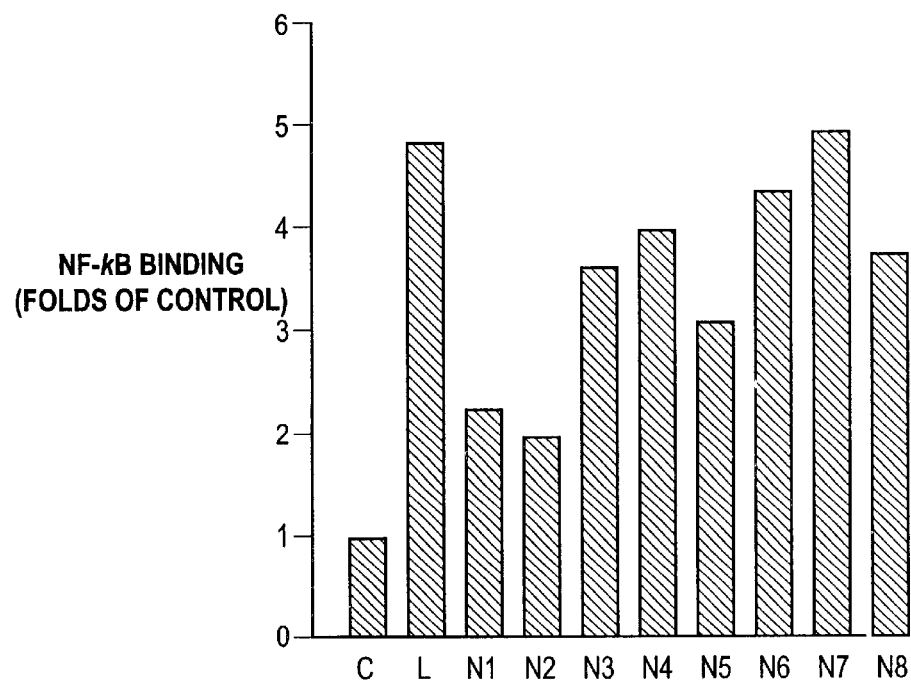
FIG. 6ii
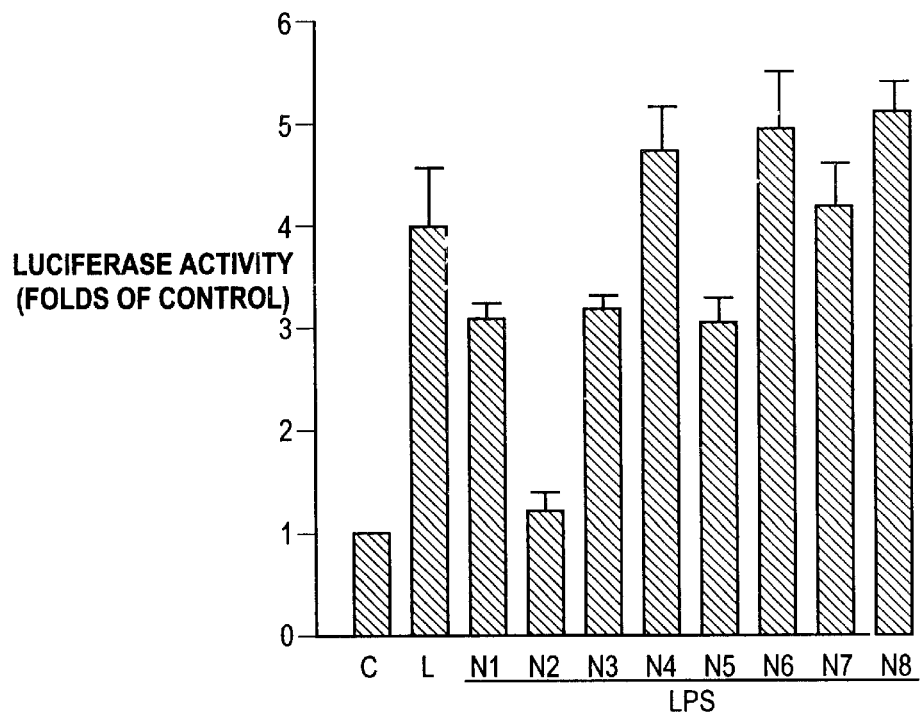
FIG. 6iii

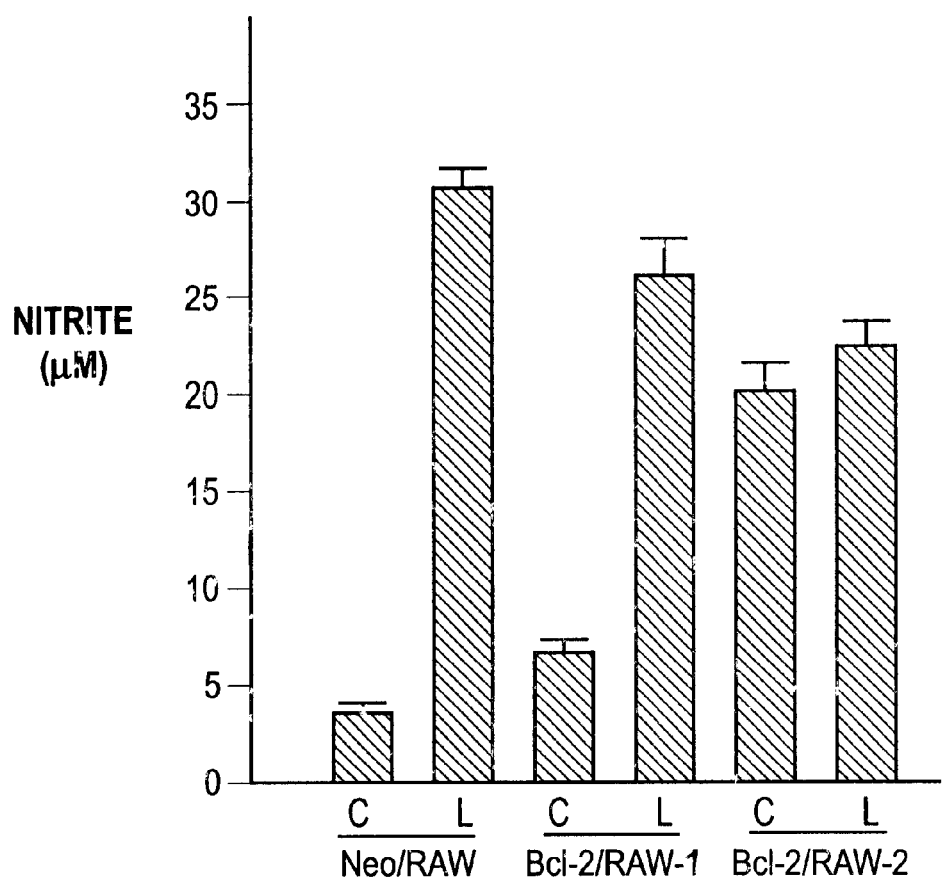

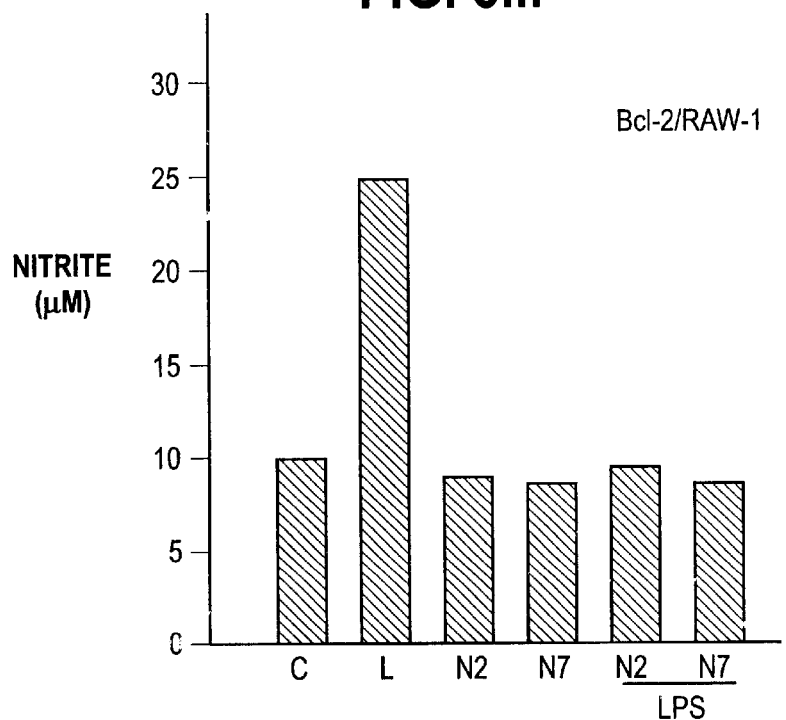
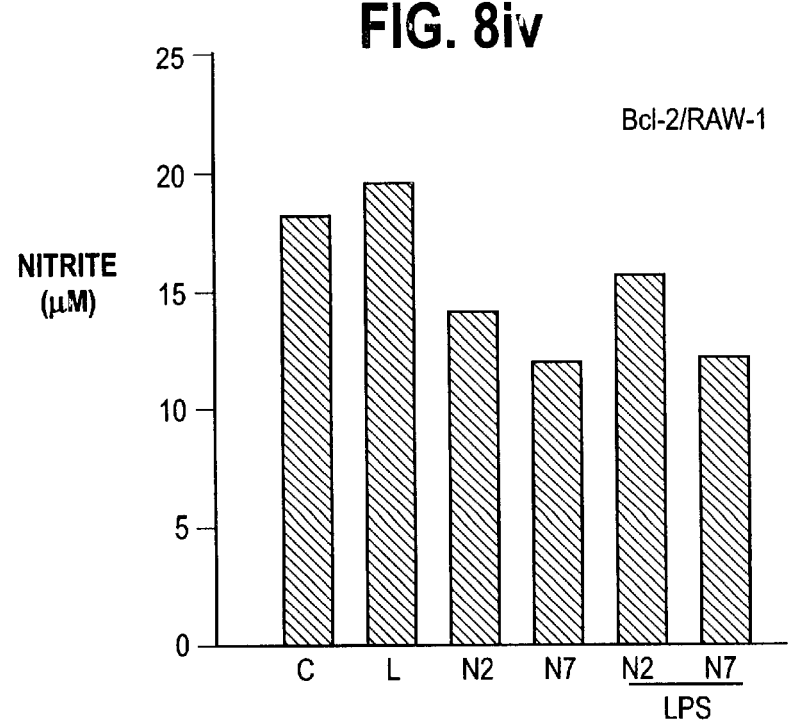

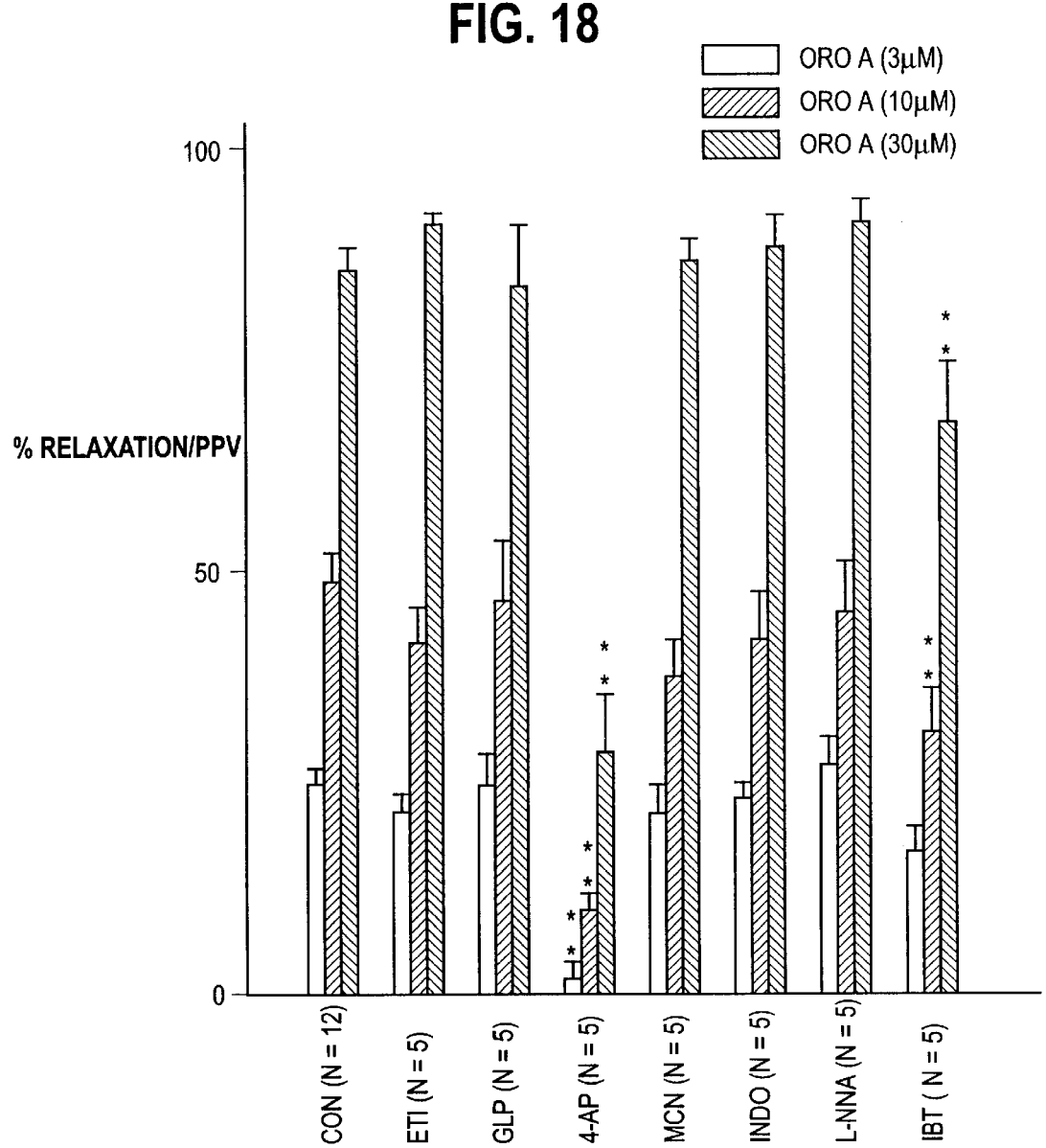

BAICALIN
MW = 446

BAICALIN
MW = 270

WOGONON
MW = 284

FLAVONES AS INDUCIBLE NITRIC OXIDE SYNTHASE INHIBITORS, CYCLOOXYGENASE-2 INHIBITORS AND POTASSIUM CHANNEL ACTIVATORS

CROSS-REFERENCE TO RELATED APPLICATIONS

This application is a continuation-in-part of co-pending U.S. Provisional Patent Application Serial No. 60/160,612, filed Oct. 20, 1999.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant Nos. HL27763 and HL47574 awarded by the National Institute of Health.

FIELD OF THE INVENTION

The present invention is directed to a method for inhibiting either iNOS or COX-2, or both in mammals using flavone compounds. The present invention is also directed to a method of activating $K^+$ channels in mammals; as well as methods for treating septic shock, treating or preventing aneurysm, inhibiting expression of angiotensin converting enzyme and reducing inflammation and related pathological changes using these compounds. Presently preferred compounds are oroxylin A (5,7-dihydroxy-6-methoxy flavone) and wogonin (5,7-dihydroxy-8-methoxy flavone).

BACKGROUND OF THE INVENTION

COX-2

Septic shock and multiple-organ failure are catastrophic consequences of an invasive infection. Septic shock has been estimated to occur in more than 500,000 cases per year in the United States alone. Septic shock is the most common cause of death in non-coronary intensive care units. As more antibiotic-resistant strains of bacteria evolve, the incidence of septic shock is expected to increase. Overall mortality rates from septic shock range from 30% to 90%. Aggressive antibiotic treatment and timely surgical intervention are the main therapies, but in many cases are insufficient. The search for new drug therapies has not been successful. For example, only small, but not statistically significant improvements in 28-day mortality compared to placebo was found when the compound Deltibant was administered to human patients suffering systemic inflammatory response syndrome and presumed sepsis (R. Stone, *J. Am. Med Assoc.*, vol. 277, pp. 482–487 (1997)).

Lipopolysaccharide (LPS) is believed to be the principal agent responsible for inducing sepsis syndrome, which includes septic shock, systemic inflammatory response syndrome, and multi-organ failure. Sepsis is a morbid condition induced by a toxin, the introduction or accumulation of which is most commonly caused by infection or trauma. The initial symptoms of sepsis typically include chills, profuse sweating, irregularly remittent fever, prostration and the like; followed by persistent fever, hypotension leading to shock, neutropenia, leukopenia, disseminated intravascular coagulation, acute respiratory distress syndrome, and multiple organ failure.

LPS, also know as endotoxin, is a toxic component of the outer membrane of Gram-negative microorganisms (e.g., *Escherichia coli, Klebsiella pneumonia, Pseudomonas aeruginosa*). Compelling evidence supports the toxic role of LPS; all pathophysiological effects noted in humans during Gram-negative sepsis can be duplicated in laboratory animals by injection of purified LPS. The mechanism by which LPS activates responsive cells is complex and not fully understood. The host response to Gram-negative bacterial infection depends on effector cell recognition of the bacteria, LPS, or both and involves both serum proteins and cell membrane receptors. When bacteria and LPS are removed via endocytosis and phagocytosis by reticuloendothial cells, concomitant activation of the host immune response by LPS results in the secretion of cytokines by activated macrophages, which in turn can trigger the exaggerated host responses associated with septic shock.

The normal immune response begins when neutrophils squeeze through the blood-vessel walls searching for bacterial pathogens in the surrounding tissue. Neutrophils can kill bacteria directly by releasing toxic chemicals or enzymes, such as elastase or collagenase. The neutrophils also attract other leukocytes to the area, including lymphocytes, macrophages, and monocytes, the last two of which release powerful immune-response activators called cytokines. The cytokines, in turn, stimulate more immune cell activity and increase the number of cells coming to the area by making the blood-vessel wall more permeable. Then, as the number of bacteria decreases, other cytokines signal to bring the normal immune response to an end.

If the cutoff mechanism fails, however, sepsis can begin. In sepsis, humoral and cellular mediators cascade in a process that becomes at least temporarily independent of the underlying infection. Excess neutrophils and macrophages are drawn to the site of infection, releasing excess immune-stimulating cytokines, eventually triggering the release of substances that damage the blood-vessel wall. More monocytes and macrophages come to the site and release more cytokines. Eventually, the blood vessels are so damaged and leaky that blood pressure falls and the blood can no longer supply nutrients to the body's organs. Entire organs can begin to shut down. Many patients die after losing the function of two or more organs.

Two cytokines that play an important role in sepsis are interleukin-1 (IL-1) and tumor necrosis factor-alpha (TNF alpha). These two polypeptides can raise body temperature, increase the expression for adhesion molecules on neutrophils and endothelial cells (promoting adhesion of leukocytes), stimulate the production of vasodilating prostaglandins (thus increasing the permeability of blood vessels), trigger the release of other cytokines, stimulate neutrophils, and activate fibroblasts. All these processes enhance the probability of organ failure seen in severe septicemia. Drug therapies that target only one of these two cytokines have proved ineffective (See Stone). Drug therapies that are effective against general inflammatory responses have not proven to be effective against the cascading acute inflammation that produces septicemia. There is a need for drugs that can inhibit this cascading system at the beginning steps of production of IL-1 and TNF alpha.

Other important cytokines, chemokines, and other proteins having proinflammatory activity include interferon-gamma (IFN gamma), interleukin-6 (IL-6), macrophage chemotactic protein (MCP), inducible nitric oxide synthetase (iNOS), mitogen-activated protein kinases (MAPKs), macrophage inflammatory protein, KC/CINC (growth related gene), tissue factor (TF), granulocyte-macrophage-colony stimulating factor (Gm-CSF) and phosphotyrosine phosphatase (PTPase).

Prostaglandins are also involved in the proinflammatory response; e.g., prostaglandins increase the permeability of the blood-vessel wall. Cyclooxygenase (COX; prostaglandin endoperoxide synthase) catalyzes the conversion of arachidonic acid to prostaglandin (PG) endoperoxide (PGH2), which is the rate limiting step in prostaglandin biosynthesis. Two isoforms of COX have been cloned from animal cells: the constitutively expressed COX-1, and the mitogen-inducible COX-2. Prostaglandins produced as a result of the activation of COX-1 may have physiological functions such as the antithrombogenic action of prostacyclin released by the vascular endothelium, and the cytoprotective effect of PGs produced by the gastric mucosa. However, COX-2 is the enzyme expressed following the activation of cells by various proinflammatory agents including cytokines, endotoxin and other mitogens. These observations suggest that COX-2 instead of COX-1 may be responsible for inducing production of the prostaglandins involved in inflammation. Only a few pharmacological agents that suppress the expression of COX-2 without affecting COX-1 have been identified, for example, glucocorticoids and radicicol. However, these agents have undesirable side effects.

There is a need for compounds that selectively inhibit COX-2, and that act as potent anti-inflammatory agents, with minimal side effects. To prevent septicemia, such a compound should also inhibit the production of a wide variety of proinflammatory cytokines, especially TNF alpha and IL-1, chemokines, and protein-tyrosine kinases.

Nitric Oxide (NO) was originally identified in vascular endothelial cells (Palmer et al. (1987) *Nature* 327:524–526 and Palmer et al.(1988) *Nature* 333:664–666) and has been identified as being identical to endothelium-derived relaxing factor (Moncada et al. (1989) *Biochem. Pharmacol.* 38:1709–1715; Furchgott (1990) *Acta Physiol. Scand.* 139:257–270 and Iganarro (1990) *Annu. Rev. Phamacol. Toxicol.* 30:535–560). Besides endothelial cells, NO formation has been demonstrated in macrophages (Hibbs et al. (1987) *Science* 235:473–476 and Marletta et al. (1988) *Biochemistry* 27:8706–8711), neutrophils (McCall et al. (1989) *Biochem. J.* 262:293–297; Salvemini et al. (1989) *Proc. Natl. Acad. Sci. USA* 86:6328–6332 and Wright et al. (1989) *Biochem. Biophys. Res. Commun.* 160:813–819), some tumor cells (Amber et al. (1988) *J. Leuk. Biol.* 44:58–65), adrenal glands (Palacios et al. (1989) *Biochem. Biophys Res. Commun.* 165:802–809). Kupffer cells (Billiar et al. (1989) *J. Exp. Med.* 169:1467–1472) and in brain tissue (Garthwaite et al. (1988) *Nature* 336:385–388; Knowles et al. (1989) *Proc. Natl. Acad. Sci.USA* 86:5159–5162 and Bredt and Snyder (1989) *Proc. Natl. Acad. Sci. USA* 86:9030–9033).

Endothelium-derived NO relaxes the smooth muscles of blood vessels (Palmer et al. (1987) *Nature* 327:524–526 and Ignarro et al. (1987) *Proc. Natl. Acad. Sci. USA* 84:9265–9269) and inhibits platelet adhesion (Radomski et al. (1987) *Biochem. Biophys. Res. Commun.*, 148:1482–1489). NO production by cocultures of Kupffer cells and hepatocytes mediates inhibition of hepatocyte protein synthesis (Billar et al. (1989) *J. Exp. Med.* 169:1467–1472). NO is responsible for mediating the cytotoxic effects of macrophages and neutrophils (Hibbs et al. 91987) *J. Immunol.* 138:550–556). NO has also been shown to be a major neuronal messenger in the brain (Bredt and Snyder (1989) *Proc. Natl. Acad. Sci. USA* 86:9030–9033). The mediation of functions of tissues as diverse as the brain, endothelium and blood cells indicates a wide-spread role for NO as a messenger molecule.

NO is formed by nitric oxide synthetase (NOS) from L-arginine with stoichiometric formation of L-citrulline. Studies have shown that a guanidino nitrogen of L-arginine is used to form NO (Iyengar et al. (1987) *Proc. Natl. Acad. Sci. USA* 84:6369–6373; Palmer et al. (1988) *Nature* 333:664–666 and Marietta et al. (1988) *Biochemistry* 27:8706–8711).

The formation of NO appears to involve the same or similar enzyme in brain and endothelial cells but a different enzyme in macrophages. The brain-endothelium enzyme has been found to require calcium and calmodulin for activity (Bredt and Snyder (1990) *Proc. Natl. Acad. Sci. USA* 87:682–685). The macrophage enzyme does not require calcium-calmodulin but does require tetrahydrobiopterin for activity (Tayeh and Marietta (1989) *J. Biol. Chem.* 264:19654–19658; Soo Kwon et al. (1989) *J. Biol. Chem.* 264:20496–20501).

The brain (i.e., calmodulin-dependent) NOS enzyme has been purified to homogeneity from rat brain, revealing a 150,000 kD protein (Bredt and Snyder (1990) *Proc. Natl. Acad. Sci. USA* 87:682–685).

In addition to the differences between NOS activities in brain and endothelial cells as compared to macrophages, the regulation of NOS expression appears to differ as well. The synthesis of NO does not occur in macrophages unless they have been exposed to endotoxin (e.g., bacterial lipopolysaccharide) or cytokine (e.g., interferon-gamma, -beta or alpha, tissue necrosis factor-alpha or -beta). However, in the brain and vascular endothelium, NOS is present without exposure to inducing agents (Knowles et al. (1990) *Biochem. J.* 270:833–836). The arginine derivative L-N-omega-nitroarginine ($NO_2Arg$) has been described as being a competitive inhibitor of NOS (Moore (1990) *Br. J. Pharmacol.* 99:408–412).

NO has been demonstrated to mediate neuronal relaxation of intestines (Bult et al. (1990) *Nature* 345:346–347; Gillespie et al. (1989) *Br. J. Pharmacol.* 98:1080–1082 and Ramagopal and Leighton (1989) *Eur. J. Pharmacol.* 174:297–299) and to mediate stimulation by glutamate of cGMP formation (Bredt and Snyder (1989) *Proc. Natl. Acad. Sci. USA* 86:9030–9033). Glutamate, the major excitatory neurotransmitter in the brain, acts through several receptor subtypes, some of which stimulate the formation of cGMP (Ferrendelli et al. (1974) *J. Neurochem.* 22:535–540). Glutamate, acting at N-methyl-D-aspartate (NMDA) subtype of receptors, is responsible for neurotoxic damage in vascular strokes. Selective antagonists of NMDA glutamate receptors prevent neuronal cell death in animal models of hypoxic-ischemic brain injury (Choi (1990) *J. Neurosci.* 10:2493–2501). Glutamate neurotoxicity has also been implicated in neurodegenerative disorders such as Alzheimer's and Huntington's diseases (Choi (1990) *J. Neurosci.* 10:2493–2501 and Meldrum and Garthwaite (1990) *Trends in Pharmacol. Sci.* 11:379–387).

As decribed above, nitric oxide (NO) has been shown to be an important regulatory molecule in diverse physiological functions such as vasodilation, neural communication and host defense. Molecular cloning and sequencing analysis have revealed the existence of at least three main types of NOS isoforms. NOS is present in the vascular endothelium (eNOS); in central and peripheral neurons (nNOS); and is also constitutive (cNOS). Activation is $Ca^{+2}$-dependent. Continuous release of NO by cNOS keeps the vasculature in an active state of vasodilation. Various agonists such as bradykinin and acetylcholine have been shown to trigger cNOS-mediated NO production through increasing intracellular $Ca^{+2}$. NOS in macrophages and hepatocytes, on the other hand, is inducible (iNOS) and its activation is $Ca^{+2}$-independent (Duval et al., *Mol. Pharmacol.* 50: 277–84, 1996, Yuan, T., *Febs. Lett.* 431:210–4, 1998). After exposure to endotoxin and/or cytokines, iNOS can be induced in various cells such as macrophages, Kupffer cells, smooth muscle cells and hepatocytes. The induced iNOS catalyzed the formation and release of a large amount of NO, which play a key role in the pathophysiology of a variety of diseases including septic shock (Pedoto, A. et al., *Crit. Care Med.* 26:2021–8, 1998). NO production catalyzed by iNOS therefore may reflect the degree of inflammation and provides a measure by which effects of drugs on the inflammatory process can be assessed.

It is known that inhibition of either iNOS or COX-2 enzymes prevents aneurysm (Miralles, M. et al. *J. Vasc. Surg.* May 1999, Vol. 5, pp. 884–892; and Fukuda, S. *Circulation*, May 2000, 101 (21) pp. 2532–2538).

Expression of cyclooxygenase-2 (COX-2) in various tissue preparations following LPS treatment has also been reported (Quan, N. et al., *Brain Res.* 802:189–197; Lee, S. H. et al., *J. Biol. Chem.* 267: 25934–25938, 1992). This enzyme also is considered to play a major role in inflammatory process by catalyzing the production of prostaglandins.

Compounds which inhibit iNOS or COX-2 would be useful anti-inflammatory agents as has been described above; and a compound which inhibits or prevents induction of both enzymes at the same time should be particularly useful. To date, compounds which inhibit both enzymes have not been identified.

Therefore, one object of the invention is to identify anti-inflammatory agents. A further object of the invention is to identify compounds which inhibit induction of both iNOS and COX-2.

Potassium Channels

Four types of $K^+$ channels have been described in vascular and nonvascular smooth muscle. These are: (1) calcium-activated (2) voltage-dependent (also called delayed rectifier) (3) ATP-sensitive and (4) inwardly rectifying $K^+$ channels. Calcium-activated $K^+$ channels ($K_{Ca}$ channels) have been found in virtually every type of smooth muscle. These $K^+$ channels are activated by increasing levels of intracellular calcium. They may also be activated by membrane depolarization, although this mechanism also requires calcium at physiologic membrane potentials. Calcium-activated $K^+$ channels are thought to be the most abundant in vascular smooth muscle, with up to $10^4$ channels estimated to be present per cell (Nelson and Quayle, "Physiological Roles and Properties of Potassium Channels in Arterial Smooth Muscle", *Am. J. Physiol.* 268 (4Pt 1): C799–822, 1995).

One of the important physiological roles of $K_{Ca}$ channels is regulation of smooth muscle or myogenic tone. Elevation of intravascular pressure depolarizes smooth muscle cells in resistance arteries and causes vasoconstriction. This tone has been referred to as "myogenic tone" and is a major contributor to peripheral resistance. $K_{Ca}$ channels play an important role in the control of myogenic tone. It has been proposed that pressure-induced membrane depolarization and increases in intracellular $Ca^{2+}$ activate $K_{Ca}$ channels. Activation of $K_{Ca}$ channels would increase $K^+$ efflux, which would counteract the depolarization and constriction caused by pressure and vasoconstrictors. Activation of $K_{Ca}$ channels acts as a negative feedback mechanism to limit vasoconstriction.

$K_{Ca}$ channels are regulated by endogenous vasoactive substances. Most vasoconstrictors (e.g. norepinephrine, angiotensin II, endothelin, and serotonin) depolarize vascular smooth muscle. It is conceivable that inhibition of $K_{Ca}$ channels contributes to this membrane depolarization. Recently, angiotensin II and a thromboxane A2 agonist (U-46619) have been shown to inhibit $K_{Ca}$ channels from coronary artery smooth muscle. Muscarinic receptor stimulation has been shown to inhibit $K_{Ca}$ channels in airway and colonic smooth muscle. (Faraci and Sobey, "Role of Potassium Channels in Regulation of Cerebral Vascular Tone", *J. Cereb. Blood Flow Metab.* 18 (10): 1047–63, 1998).

Activation of $K_{Ca}$ channels would tend to hyperpolarize smooth muscle and lead to muscle relaxation. β-Adrenergic stimulation activates $K_{Ca}$ channels in airway smooth muscle cells and thus may contribute to β-adrenergic bronchodilation. This activation of $K_{CA}$ channels in airway and coronary artery smooth muscle cells appears to be caused by phosphorylation mediated by an adenosine 3',5'-cyclic monophosphate (cAMP)-dependent protein kinase as well as a direct G protein pathway. Recent evidence indicates that guanosine 3',5'-cyclic monophosphate (cGMP)-dependent protein kinase can also activate $K_{CA}$ channels in smooth muscle cells isolated from cerebral and coronary arteries. Nitric oxide can activate cGMP-dependent protein kinase through stimulation of guanylyl cyclase and elevation of cGMP. Furthermore, nitric oxide has also been reported to directly activate $K_{CA}$ channels in aortic smooth muscle. Vasorelaxation of some vascular beds (e.g., mesenteric and cerebral arteries) in response to nitric oxide appears to involve activation of $K_{CA}$ channels.

Like calcium-activated $K^+$ channels, voltage-dependent $K^+$ channels are activated in response to membrane depolarization, but this process occurs independent of the intracellular calcium concentration. Because both voltage-dependent and calcium-activated $K^+$ channels are activated by depolarization, 4-aminopyridine (4-AP) can be used to distinguish responses mediated by either channel. Tetraethylammonium (TEA) is a poor inhibitor of voltage-dependent $K^+$ channels unless very high concentrations are used. The estimated number of voltage-dependent $K^+$ channels per cell in arteries is about $10^3$.

Compared with other $K^+$ channels, much less is known about the functional importance of voltage-dependent $K^+$ channels. It has been suggested that activity of voltage-dependent $K^+$ channels influence resting cerebral vascular tone. These $K^+$ channels are also activated by increases in arterial blood pressure. Recent studies suggest that activation of voltage-dependent $K^+$ channels may contribute to mechanisms that produce cerebral vasorelaxation in response to NO and endothelium-derived hyperpolarizing factor (EDHF) (Faraci and Sobey, 1998).

There are three physiological roles of $K_v$ channels which include: (1) Repolarization of the action potential. Despite the wide distribution of $K_v$ channels, relatively few studies have been conducted on the physiological role of this channel in arterial smooth muscle. Because the channel is activated by depolarization, it may be involved in action potential repolarization in electrically excitable smooth muscle preparations such as the portal vein, and this is a principal function of the channel in other excitable cells, including neurons and cardiac muscle. However, most arteries generally respond to stimuli with graded membrane potential changes, and therefore $K_v$ channels are unlikely to be involved in action potential repolarization in these arteries. (2) Regulation of the membrane potential. $K_v$ channels provide an important $K^+$ conductance in the physiological membrane potential range in arteries that do not generate action potentials. Activation of $K_v$ channels by membrane depolarization, e.g., in response to pressurization or vasoconstrictors, may limit membrane depolarization. $K_v$ channels may also be directly modulated by vasoconstrictors and vasodilators, and a 4-AP-sensitive $K^+$ current is inhibited by a histamine $H_1$ receptor agonist in coronary arteries. It was suggested that inhibition of the 4-AP-sensitive current occurred as a result of increased intracellular $Ca^{2+}$ concentration through intracellular $C^{2+}$ release. A related observation is that intracellular $Mg^{2+}$ (10 mM) inhibits $K_v$ currents positive to −15 mV in arterial smooth muscle cells. (3) hypoxic pulmonary vasoconstruction. Pulmonary arteries constrict in hypoxia, which minimizes blood perfusion in poorly ventilated areas of the lung. This hypoxic vasoconstriction contrasts with the hypoxic vasodilation seen in many small systemic arteries and which may involve an activation of other types of $K^+$ channels. During hypoxia, pulmonary arteries depolarize and may generate action potentials. The resulting pulmonary vasoconstriction is abolished by removal of extracellular $Ca^{2+}$ and by $Ca^{2+}$ channel antagonists such as verapamil, suggesting that $Ca^{2+}$ entry through voltage-dependent $Ca^{2+}$ channels is important in the hypoxic response.

Recent studies suggest a role for $K^+$ channels in hypoxia-induced membrane depolarization and constriction. $K^+$ channel inhibitors such as $TEA^+$ and 4-AP increase tone in isolated pulmonary vessels and increase perfusion pressure in the isolated perfused lung. Thus $K^+$ channels contribute to the membrane potential in pulmonary arteries as they do in systemic arteries. Because $K^+$ channels regulate the membrane potential of pulmonary smooth muscle, hypoxia may depolarize by inhibiting $K^+$ channels. It has recently been directly shown that hypoxia inhibits voltage-activated $K^+$ currents in these arteries. The voltage dependence of the hypoxia-sensitive channel suggests that it is a member of the $K_v$ or $K_{Ca}$ families. A number of mechanisms have been proposed to link hypoxia to channel inhibition. $K_{Ca}$ channels in rat pulmonary arterial myocytes are activated by intracellular ATP. Therefore a fall in intracellular ATP during hypoxia may inhibit this channel. However, the ATP connection in smooth muscle cells is generally well conserved during hypoxia. Cellular redox status has also been proposed as the link between hypoxia and $K^+$ channel activity, and an increase in cellular reducing agents causes inhibition of $K^+$ channels in pulmonary arteries.

One key characteristic of ATP-sensitive $K^+$ channels ($K_{ATP}$) is that their activity may reflect the metabolic state of the cell. These $K^+$ channels are sensitive to intracellular ATP, which inhibits channel activity. Dissociation of ATP from the channel results in channel opening and membrane hyperpolarization. Other metabolically related stimuli, including reductions in $PO_2$ or pH, also open the channel and produce vasorelaxation. It is estimated that a few hundred ATP-sensitive $K^+$ channels are present per cell in arteries. The number is much less than that for calcium-activated $K^+$ channels.

$K_{ATP}$ channels have several physiological roles. The channel is activated by a number of vasodilators, and the associated membrane hyperpolarization causes part of the resulting vasodilation in many cases. The $K_{ATP}$ channel may also be inhibited by vasoconstrictors which would tend to cause depolarization and constriction. The channel is involved in the metabolic regulation of blood flow; it is activated in conditions of increased blood demand, e.g., in hypoxia, either by release of vasodilators from the surrounding tissue or as a direct result of hypoxia on the vascular smooth muscle cells. Finally, the channel may be active in the resting state, because inhibition of $K_{ATP}$ channels can lead to increased resistance to blood flow in some vascular beds.

Inwardly rectifying $K^+$ channels ($K_{IR}$ channels) are present in a variety of excitable and nonexcitable cells, including some arterial smooth muscle cells. The name of this channel comes from the observation that the membrane potential is controlled, e.g., by voltage clamp of the cell, inward currents through the $K_{IR}$ channel (movement of $K^+$ from the extracellular solution into the cell) are larger than outward currents. This is because the $K_{IR}$ channel is activated by membrane hyperpolarization, in contrast to $K_V$ and $K_{Ca}$ channels, which are activated-by membrane depolarization.

Although outward currents through the $K_{IR}$ channel are small, in most physiological situations the cell membrane potential is positive to the $E_K$, providing an electrochemical gradient for $K^+$ to leave the cell. The $K_{IR}$ channel therefore normally conducts an outward hyperpolarizing membrane current. From a physiological standpoint, these small outward currents are therefore of considerable interest. Outward $K^+$ movement through the cardiac muscle $K_{IR}$ channel is limited by voltage-dependent channel closure on membrane depolarization and may also involve block of outward current through the channel by intracellular $Mg^{2+}$. However, the role of intracellular $Mg^{2+}$ is complex because channels that are blocked are unable to undergo voltage-dependent closure.

The physiological roles of the $K_{IR}$ channel in cells other than smooth muscle include regulating the resting membrane potential, preventing membrane hyperpolarization to values more negative than the $E_k$ by the electrogenic $Na^+$-$K^+$-ATPase, and minimizing cellular $K^+$ loss and therefore energy expenditure during sustained membrane depolarization. The roles of the $K_{IR}$ channel in arterial smooth muscle are incompletely understood but may include some of the functions such as mediates $K^+$-induced dilations and regulation of membrane potential.

In summary, activation of $K^+$ channels in arterial smooth muscle cells can increase blood flow and lower blood pressure through vasodilation. Inhibition of $K^+$ channels in arterial smooth muscle leads to vasoconstriction. Four types of $K^+$ channels ($K_V$, $K_{Ca}$, $K_{ATP}$ and $K_{IR}$ channels) have been identified to regulate the membrane potential of vascular and nonvascular smooth muscle cells.

$K_{Ca}$ channels in arterial smooth muscle cells respond to changes in intracellular $Ca^{2+}$ to regulate membrane potential. $K_{Ca}$ channels appear to play a fundamental role in regulating the degree of intrinsic tone of resistance arteries. These channels help regulate arterial responses to pressure and vasoconstrictors.

$K_V$ channels regulate membrane potential in response to depolarizing stimuli, and these channels may be involved in hypoxia-induced membrane depolarization in the pulmonary vasculature.

$K_{ATP}$ channels are targets of a number of vasodilating stimuli, including hypoxia and adenosine. A variety of antihypertensive drugs (e.g., minoxidel sulfate, diazoxide, lemakalim, pinacidil) act through activation of $K_{ATP}$ channels. Pathological conditions such as hypotension associated with septic shock may involve excessive activation of $K_{ATP}$ channels.

$K_{IR}$ channels appear to mediate external $K^+$-induced hyperpolarizations and dilations of resistance arteries and thus provide a mechanism for linking the metabolism of surrounding cells (e.g., neurons) to blood flow.

All of these K+ channel types may be involved in the actions of a variety of vasodilators and vasoconstrictors, and their function may be altered in diseases. K+ channels in arterial smooth and nonvascular smooth muscle (such as uterine and pulmonary) muscle are important modulators of blood vessel diameter, and muscle tone. Our results indicate that oroxylin A is a $Ca^{2+}$— activated K+ channel opener, but is not a $K_{ATP}$ channel opener. Preliminary results further indicate that oroxylin A may activate other K+ channels such as $K_V$ or $K_{IR}$ channels.

BRIEF SUMMARY OF THE INVENTION

The present invention is directed to methods for inhibiting expression of iNOS, COX-2, or both using a flavone and pharmaceutically acceptable salts thereof. The present invention is also directed to a method for activation of potassium channels by flavones; a method for treating septic shock with flavones; a method for inhibiting expression of angiotensin converting enzyme with flavones; a method for reducing inflammation and related diseases with flavones; and a method for treating or preventing aneurysms with flavones.

More particularly, the present invention is directed to the use of compounds of the formula I

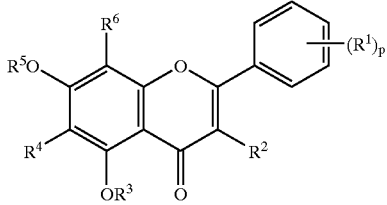

Formula I wherein p is an integer of zero to five;
$R^1$, at each occurrence, is independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-CO($C_1$–$C_3$ alkyl), $C_1$–$C_3$alkylamino, alkenylamino, alkynylamino, di($C_1$–$C_3$ alkyl)amino, COOH, C(O)O—($C_1$–$C_3$ alkyl), C(O)NH—($C_1$–$C_3$ alkyl), C(O)N($C_1$–$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, heterocyclylalkyl, sulfonamido, carbamate, aryloxyalkyl and C(O)NH (benzyl);
$R^2$, $R^4$ and $R^6$ are each independently selected from the group consisting of hydrogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-C(O)($C_1$–$C_3$ alkyl), $C_1$–$C_3$alkylamino, alkenylamino, alkynylamino, di($C_1$–$C_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, halogen and aryloxyalkyl; and
$R^3$ and $R^5$ are each independently selected from the group consisting of hydrogen, $C_1$–$C_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;
wherein $R^1$, $R^2$, $R^3$, $R^4$, $R^5$ and $R^6$ are unsubstituted or substituted with at least one electron donating or electron withdrawing group;
and pharmaceutically acceptable salts thereof in the methods described above. Presently preferred flavones are 5,7-dihydroxy-6-methoxy flavone (oroxylin A, wherein p is zero, $R^2$, $R^3$, $R^5$ and $R^6$ are hydrogen, and $R^4$ is methoxy for formula I above) and 5,7-dihydroxy-8-methoxy flavone (wogonin, wherein p is zero, $R^2$, $R^3$, $R^4$ and $R^5$ are hydrogen, and $R^6$ is methoxy for formula I above). For the preferred flavones, when p=zero, the phenyl ring (substituted by $(R^1)_p$ in formula I) is unsubstituted. The unsubstituted phenyl ring is defined herein either as when p is five and $R^1$ is hydrogen, or when p=0. Useful derivatives of the compounds of Formula I include esters, carbamates, animals, amides, optical isomers and pro-drugs thereof.

For the practice of any aspect of this invention, a bactericidal amount of an antibiotic may be co-administered with the flavone.

BRIEF DESCRIPTION OF THE DRAWINGS

FIG. 2 shows effects of various concentrations of the FIG. 1 polyphenols on LPS-induced nitrite production in RAW264.7 macrophages.

FIG. 18 shows effects of several compounds on relaxation induced by oroxylin A in porcine cerebral arteries without endothelial cells precontracted with U46619. Relaxation was estimated as a percentage of maximum relaxation induced by papaverine (PPV, 300 μM). Values are means±S.E.M. n=5 for each drug examined. *P<0.05 and **P<0.01 indicate significant differences from the respective controls.

DETAILED DESCRIPTION OF THE INVENTION

Definition of Terms

Figure 1A:
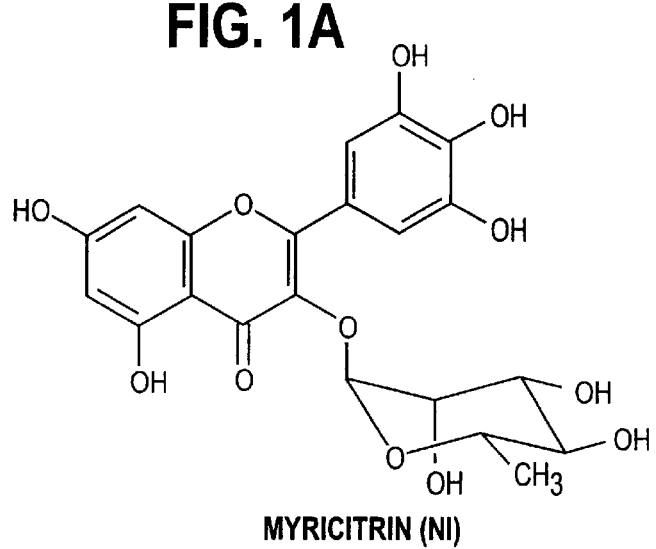
FIG. 1 shows the chemical structures of the polyphenols used in the study, including two flavonoids (myricitrin, N1; oroxylin A, N2) four ellagitannins (penta-O-galloyl-β-glucopyranose, N3; woodfordin C, N4; onothein B, N5; cuphiin D1, N6), and two anthraquinones (emodin, N7; physcion, N8).
Figure 1B:
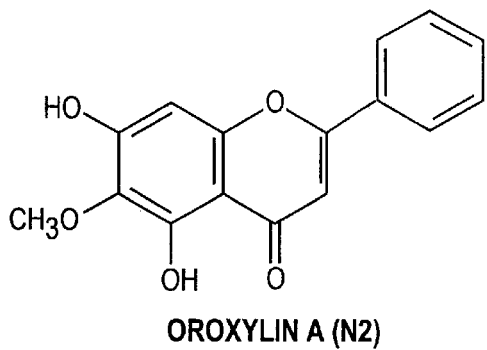
Figure 1C:
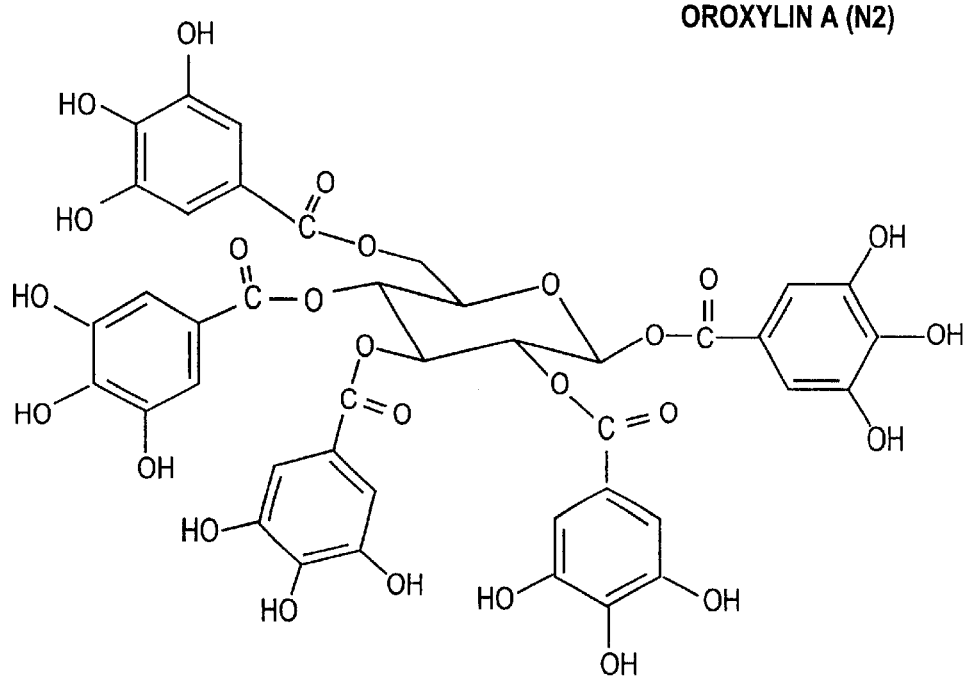
Figure 1D:
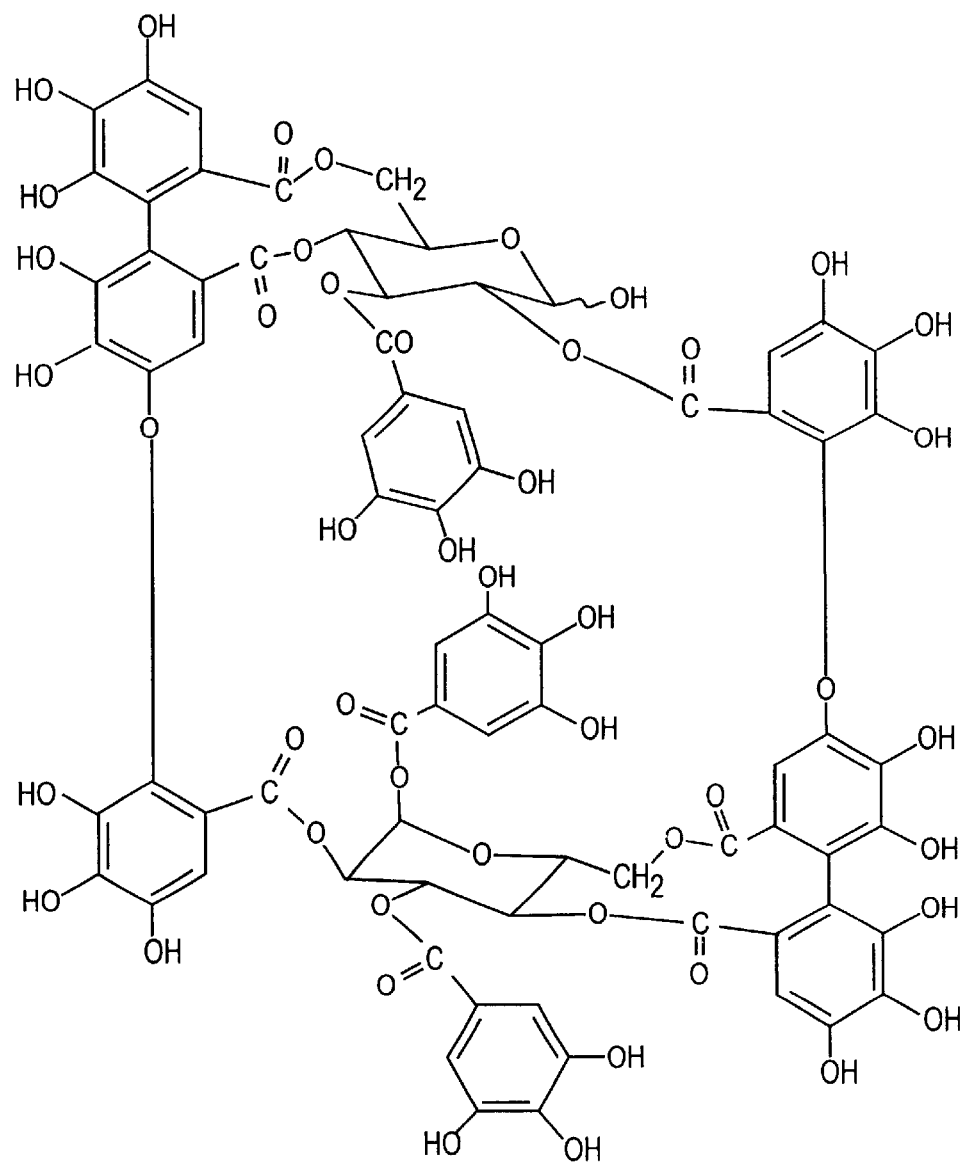
Figure 1E:
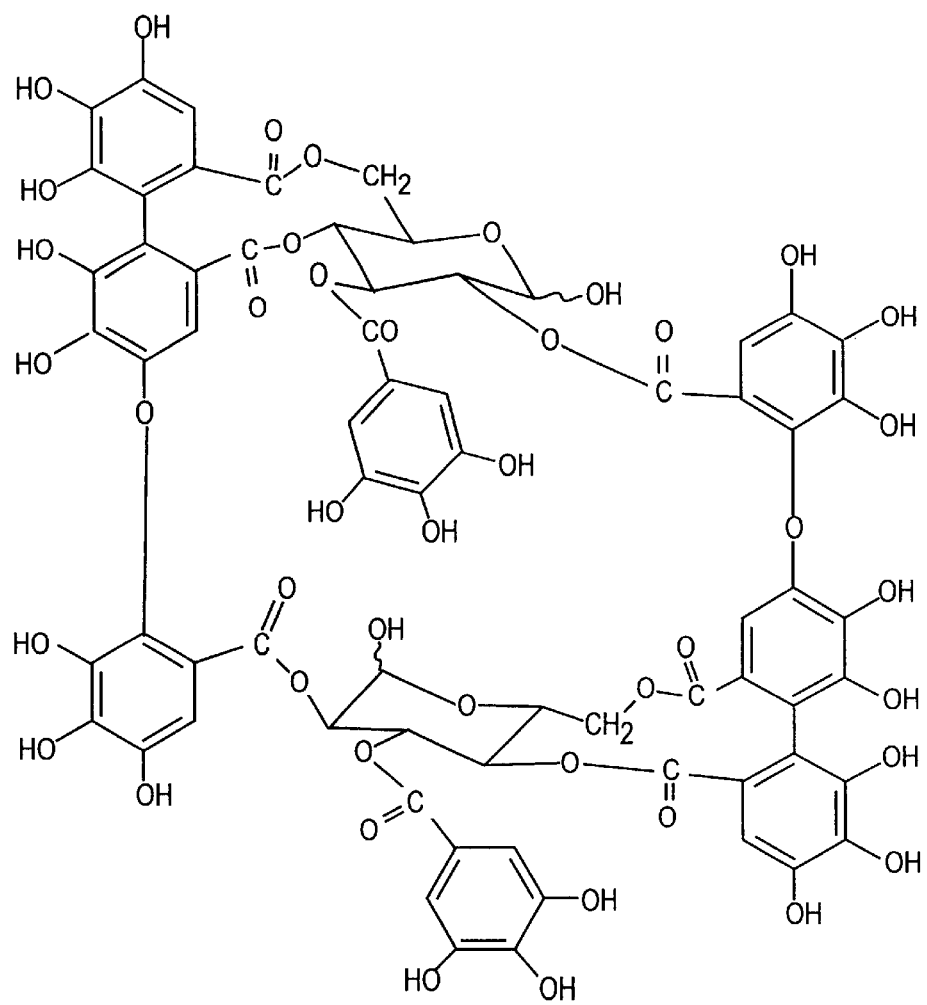

The term "alkyl" as used herein alone or in combination refers to a straight or branched, substituted or unsubstituted chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination, refers to a straight-chain or branched-chain, substituted or unsubstituted alkenyl radical. Examples of such radicals include, but are not limited to, ethenyl, E- and Z-pentenyl, decenyl and the like.

The term "alkynyl", alone or in combination, refers to a straight or branched chain alkynyl radical. Examples of such radicals include, but are not limited to, ethynyl, propynyl, propargyl, butynyl, hexynyl, decynyl and the like.

The term "aliphatic acyl" as used herein, alone or in combination, refers to radicals of formula alkyl-C(O)—, alkenyl-C(O)— and alkynyl-C(O)— derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein alone or in combination refers to an aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. "Cycloalkyl" includes cis or trans forms. The ring system may be bridged. Furthermore, the substituents may be either in exo or endo positions in bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexyl methyl.

The term "halo" or "halogen" as used herein refers I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to a carboxylic acid radical, —C(O)OH.

The term "carboxy" as used herein refers to —C(O)—.

The term "thioalkoxy" refers to a thioether radical of formula alkyl-S—, wherein "alkyl" is as defined above.

The term "sulfonamido" as used herein refers to —SO$_2$NH$_2$.

The term "carboxaldehyde" as used herein refers to —C(O)R wherein R is hydrogen.

The terms "carboxamide" or "amide" as used herein refer to —C(O)NR$_a$R$_b$ wherein R$_a$ and R$_b$ are each independently hydrogen, alkyl or any other suitable substituent.

The term "thioalkoxy", refers to a thioether radical of formula alkyl-S—, wherein "alkyl" is as defined above.

The term "carboxaldehyde" as used herein refers to —C(O)R wherein R is hydrogen.

The term "carboxamide" as used herein refers to —C(O)NH$_2$.

The term "alkoxyalkoxy" as used herein refers to R$_b$O—R$_c$O— wherein R$_b$ is lower alkyl as defined above and R$_c$ is alkylene wherein alkylene is —(CH$_2$)$_n$'— wherein n' is an integer from 1 to 6. Representative examples of alkoxyalkoxy groups include methoxymethoxy, ethoxymethoxy, and t-butoxymethoxy among others.

The term "alkylamino" as used herein refers to R$_d$NH— wherein R$_d$ is a lower alkyl group, for example, ethylamino, butylamino, among others.

The term "alkenylamino" alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to R$_e$R$_f$N— wherein R$_e$ and R$_f$ are independently selected from lower alkyl, for example diethylamino, and methyl propylamino, among others.

The term "amino" as used herein refers to H$_2$N—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "arylamino", alone or in combination, refers to a radical of formula aryl-NH—, wherein "aryl" is as defined above. Examples of arylamino radicals include, but are not limited to, phenylamino(anilido), naphthlamino, 2-, 3-, and 4-pyridylamino and the like.

The term "biaryl", alone or in combination, refers to a radical of formula aryl-aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "heterocycloyl", as used herein refers to radicals of formula heterocyclyl-C(O)—, wherein the term "heterocyclyl" is as defined above. Examples of suitable heterocycloyl radicals include tetrahydrofuranylcarbonyl, piperidinecarbonyl and tetrahydrothiophenecarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to a hemi-acetal of the structure R$_h$C(NR$_i$R$_j$)(NR$_k$R$_l$)— wherein R$_h$, R$_i$, R$_j$, R$_k$ and R$_l$ are each independently hydrogen, alkyl or any other suitable substituent.

The term "amide" as used herein refers to a moiety ending with a —C(O)NH$_2$ functional group.

The term "ester" as used herein refers to —C(O)R$_m$, wherein R$_m$ is hydrogen, alkyl or any other suitable substituent.

The term "carbamate" as used herein refers to compounds based on carbamic acid, NH$_2$C(O)OH.

Use of the terms "cycloalkyl", "heterocyclyl" "aryl", or "alkyl" is meant to encompass substituted and unsubstituted moieties. Substitution may be by one or more groups such as alcohols, hydroxyl, nitro, cyano, carboxy, amines, heteroatoms, lower alkyl, lower alkoxy, lower alkoxycarbonyl, acyloxy, halogens, trifluoromethoxy, trifluoromethyl or any of the substituents of the preceding paragraph or any combination of aryl, alkyl, cycloalkyl or heterocyclic groups either attached directly or by suitable linkers. The linkers are typically short chains of 1–3 atoms containing any combination of —C—, —O—, —C(O)—, —NH—, —S—, —S(O)— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Asymmetric centers may exist in the compounds of the present invention. Except where otherwise noted, the present invention contemplates the various stereoisomers and mixtures thereof.

As used herein, the term "composition" is intended to encompass a product comprising the specified ingredients in the specified amounts, as well as any product which results, directly or indirectly, from a combination of the specified ingredients in the specified amounts.

The term "aprotic solvent" as used herein refers to a solvent that is relatively inert to proton activity (not acting as a proton donor). Examples include, but are not limited to, hydrocarbons such as hexane and toluene; halogenated hydrocarbons such as methylene chloride, ethylene chloride and chloroform among others; heterocyclic compounds such as tetrahydrofuran and N-methylpyrrolidinone and ethers such as diethyl ether and bis-methoxymethylether. It will be understood by those skilled in the art that individual solvents or mixtures thereof may be preferred for specific compounds and reaction conditions, depending upon such factors as solubility of reagents, reactivity of reagents and preferred temperature ranges for example. Further discussions of aprotic solvents may be found in Organic Solvents, Physical Properties and Methods of Purification, 4th ed., John A. Riddick el al. eds., Vol II in the Techniques of Chemistry Series, 1986, among others.

"Hydroxy protecting group" as used herein, refers to an easily removable group known in the art to protect a hydroxyl group against undesirable reaction during synthetic procedures, which can then be selectively removed. The use of hydroxy protecting groups is well known in the art, and is described in detail in *Protective Groups in Organic Synthesis*, by T. Greene and P. Wuts., published by John Wiley & Sons in New York in 1991. Examples of hydroxy protecting groups include, but are not limited to, methylthiomethyl, tert-dimethylsilyl and tert-butyldiphenylsilyl among others.

The term "mammals" includes humans and other animals.

The term "heteroatom" as used herein encompasses nitrogen, sulfur and oxygen.

Abbreviations

Abbreviations which have been used in the examples which follow are: HEPES for N-2-hydroxyethylpiperazine-N'-2-ethane sulfonic acid; EDTA for ethylene diaminotetraacetic acid; DTT for dithiothreitol; iNOS for inducible nitric oxide synthase; GAPDH for glyceraldehyde 3-phosphate dehydrogenase; NBT for nitro blue tetrazolium; BCIP for 5-bromo-4-chloro-3-indolyl phosphate; PPV for papaverine; L-NNA for N-nitro-L-arginine; LPS for lipopolysaccharide; TNS for transmural nerve stimulation; TTX for tetrodotoxin; TEA for tetraethylammonium; MTT for 3-(4,5-dimethyl-thizol-2-yl)-2,5-diphenyl tetrazolium bromide; DMSO for dimethyl sulfoxide and COX-2 for cyclooxygenase-2. Flavone is 2-phenylchromone; use of the term flavone and flavones herein encompasses 2-phenylchromone derivatives such as narigenin, 5,6-dimethoxy-7-benzyloxy-flavone, wogonin, 5,7-dihydroxy-6-methoxyflavone (oroxylin A), and 5,6,7-trihydroxyflavone. Use of the term flavone herein also encompasses iso-flavones.

Amino acids are abbreviated as follows: C for L-cysteine; D for L-aspartic acid; E for L-glutamic acid; G for glycine; H for L-histidine; I for L-isoleucine; L for L-leucine; N for L-asparagine; P for L-proline; Q for L-glutamine; S for L-serine; A for L-adenine; T for L-threonine; V for L-valine, and W for L-tryptophan.

Diseases which may be treated by compounds which inhibit either iNOS or COX-2 or both include the following: heart disease, asthma, arthritis, stroke, migraine disease, colon cancer, Alzheimer's disease, aneurysms, stopping uterine contractions (tocolytic effect), sepsis syndrome and cancer. Organ transplantation may also be facilitated by such inhibitors.

The compounds useful for the practice of the method, as well as in the compositions described above, may be obtained either by synthesis, or by extraction from plants, which are both well known to those skilled in the art.

The plants that active ingredients can be extracted from are known for use in traditional Chinese herbal remedies. For example, in U.S. Pat. No. 5,447,719, Scutellaria root was extracted to obtain an oroxylin derivative, which was useful as a beta-glucuronidase inhibitor. Isolation techniques are also disclosed in "Oroxylin", *J. Chem. Soc.,* 79, 954, 1901;. and "The Constitution of Oroxylin-A, a Yellow Colouring Matter from the Root-bark of *Oroxylin Indicum*", *J. Chem. Soc.,* 1936, 591.

Synthetic procedures to make flavones are disclosed in "Ring Isomerization of Flavones, New Synthesis of Oroxylin-A and 7-Methyl-Oroxylin-A", *Tet. Let.,* 48, 1985, pp. 4281–4282; and "Nuclear Oxidation in Flavones and Related Compounds", *Proc. Indian Acad. Sci.,* 29A. 1949.

As to therapeutic uses for flavones, flavone acetic acid was cited as an inhibitor of cyclooxygenase in U.S. Pat. No. 5,071,872; and as a nitric oxide scavenger in U.S. Pat. No. 5,612,310. Some flavone derivatives have been described as having anti-inflammatory properties in U.S. Pat. Nos. 5,013, 852; 5,889,003 and 5,849,733.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: p. 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

Dosage forms for topical administration of the flavones include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions used in the method of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds used in the method of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds used in the method of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The compounds of the present invention may be co-treated with an antibiotic. As used herein, the term "antibiotic" refers to a chemical substance which possesses activity against a specific microorganism. Examples of suitable antibiotics include penicillin, cephalosporin, vancomycin, polymyxin B, aminoglycosides, tetracyclines, chloramphenicol, erythromycin, clindamycin, rifampin, metronidazole, quinolones and sulfonamides among others.

For the practice of the method, the compounds of the present invention may be formulated together with one or more non-toxic pharmaceutically acceptable carriers. The pharmaceutical compositions can be specially formulated for oral administration in solid or liquid form, for parenteral injection or for rectal administration.

The pharmaceutical compositions used in the method of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Moreover, pharmaceutical compositions used in the method of the present invention may include a physiologically tolerable diluent. The method of the present invention includes one or more compounds as described above formulated into compositions together with one or more nontoxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions used in the method can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds used in the method of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 el seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The present invention contemplates both flavones of the present invention, as well as flavones formed by in vivo conversion to compounds of the present invention.

Compounds used in the method of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds used in the method of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The ability of the method of the present invention to prevent inflammation is described in detail hereinafter in the Examples. These Examples are presented to describe preferred embodiments and utilities of the invention and are not meant to limit the invention unless otherwise stated in the claims appended hereto.

The following general information may be applied to all of the Examples.

Cells. RAW264.7, a mouse macrophage cell line, was obtained from American Type Culture Collection. Cells were cultured in RPMI-1640 medium (available from Gibco Life Technology, in Gaithersburg, Md.) supplemented with 2 mM L-glutamine, antibiotics (100 units/ml penicillin-A and 100 units/ml streptomycin) and 10% heat-inactivated fetal bovine serum (Gibco/BRL) and maintained at 37° C in a humidified incubator containing 5% $CO_2$.

Agents. Eight different polyphenolic compounds were isolated from Taiwanese and Chinese herbal plants for testing. They were classified into three types:

(1) Flavonoids: myricitrin (N1) was isolated from the leaves of Cupea hyssopifolia (Lythraceae) and oroxylin (N2) from the root of Scutellaria baicalensis (Labiatae);

(2) Ellagitannin: Penta-O-galloyl-β-glucopyranose (N3), Woodfordin C (N4), oenothein B (N5) and cuphiin D1 (N6), were isolated from the leaves of C. hyssopifolia (Lythraceae); and (3) Anthraquinones: Emodin (N7) and physcion (N8) were isolated from Rheum palmatum (Polygonaceae).

Nitrite assay. The nitrite concentration in the medium was measured as an indicator of NO production according to the Griess reaction (Kim et al., J. Immunol. 153: 4741–4748). One hundred microliters of each supernatant was. mixed with the same volume of Griess reagent (1% sulfanilamide in 5% phosphoric acid and 0. 1% naphthylethylenediamine dihydrochloride in water); absorbency of the mixture at 550 nm was determined with an enzyme-linked immunosorbent assay plate reader (Dynatech MR-7000; Dynatech Labs, Chantilly, Va.).

Western blots. Total cellular extract, cytosolic fractions (for IkB) and nuclear fraction (for p65 antibody) were prepared according to Muller et al., Immunobiology, 187, 233–256, 1993 and separated on sodium dodecyl sulfate-polyacrylamide minigels (8% for iNOS or COX-2, and 10% for IkB or p65) and transferred to immobilon polyvinylidene difluoride membranes (Millipore, Bedford, Mass.). The membrane was incubated overnight at 4° C. with 1% bovine serum albumin and then incubated with anti-iNos, COX-2, α-Tubulin monoclonal antibodies (Transduction Laboratories, Lexington, Ky.), anti-IkB or anti-p65 polyclonal antibodies (Santa Cruz Biochemicals, Santa Cruz, Calif.). iNOS, IkB, p65, Cox-2, α-Tubulin were detected by NBT and BCIP staining (Sigma Chemical Co., St. Louis, Mo.).

Northern blot analysis. Total RNA (20 µg/lane) were separated by electrophoresis on 1.2% agarose gel containing 6.7% formaldehyde and transformed to a Hybond-N nylon membrane (American Life Science) in 20×standard saline citrate (3 M sodium chloride and 0.3 M sodium citrate, pH 7.0). After heating at 80° C. for 2 hours and prehybridization for 4 hours, the filters were hybridized with $^{32}$P-labeled murine iNOS cDNA probes at a concentration of $3 \times 10^6$ cpm/ml for 16–18 hours at 42° C. The probe was labeled with [α-32P] dCTP by using Random Primer labeling kit (Stratagene, La Jolla, Calif.). Then, the filters were washed, dried and autoradiographed with Kodak-X-Omat XAR-film using intensifying screens at −80° C.

Transient transfections and luciferase activity assay. All transfectants were carried out using standard calcium phosphate precipitation procedure. For luciferase activity assays, RAW264.7 macrophages were transfected with 2 μg reporter plasmid containing 5×NF-kB sites in its enhancer element (STRATAGENE, La Jolla, Calif.). After 48–72 hours, cells were treated with LPS alone or LPS plus each indicated compound for 4 hours, then cells were lysed by lysis. buffer (0.5 M HEPES, pH. 7.4; 1 mM $CaCl_2$; mM $MgCl_2$; 1% Trixton X-100). Analysis of luciferase activity was performed using a a Luciferase reporter gene assay kit (Packard BioScience Company). Establishment of Bcl-2/RAW264.7 macrophage cells. RAW264.7 cells expressing Bcl-2 were created by electroporation (model T800; BTx, San Diego, Calif.) of RAW264.7 cells with Bcl-2 expression vector pC-Δj-bcl-2 (a gift from Dr. S. -F. Yang for Institute of Molecule Biology, Academic Scinica, Taiwan) or neo-controlled vector. pC-Δj-bcl-2, the expression vector that carries the human Bcl-2 cDNA under control of the SV40 promoter/enhancer sequence, was developed and has recently been used in our previous study, Chen, Y. C., *J. Cell Physiol.* 17, 324–333, 1998. Briefly, cells were suspended in 1 ml N-2-hydroxyethylipiperazine-N'-2 ethanesulfonic acid (HEPES)-buffered saline containing plasmid DNA, they received electric treatment as followed; electric amplitude, 350V; pulse width, 99 μs. Stable transfectants resistant to genisticin G418 (Gibco BRL, Eggenstein, Germany) were obtained. The levels of bcl-2 expression of each clone were examined by western blotting.

Electrophoretic mobility shift assay. Nuclear and cytoplasmic extracts were prepared according to a modified method of Chen et al., *Planta Med.*, 55, 1–8, 1989. At the end of culture, the cells were suspended in hypotonic buffer A)10 mM HEPES, pH 7.6, 10 mM KCl, 0.1 mM EDTA, 1 mM DTT, 0.5 mM phenylmethylsulfonyl fluoride) for 10 minutes on ice and vortexed for 10 seconds. Nuclei were pelleted by centrifugation at 12000 g for 20 seconds. The supernatants containing cytosolic proteins were collected. A pellet containing nuclei was suspended in buffer C (20 mM HEPES, pH 7.6, 25% glycerol, 0.4 M NaCl, 1 mM EDTA, 1 mM DTT, 0.5 mM phenylmethylsulfonyl fluoride) for 30 minutes on ice. The supernatants containing the nuclear proteins were collected by centrifugation at 12000 g for 10 minutes and stored at −70° C. For electrophoretic mobility assay, each 10 μg of nuclear proteins was mixed with the labeled double-stranded NF-kB oligonucleotide, 5'-AGTTGA<u>GGGGACTTTCCC</u>AGGC-3' (SEQ ID NO:1), and incubated at room temperature for 20 minutes (underlining indicates kB consensus sequence or binding site for NF-kB/c-Rel homodimeric and hetero dimeric complexes). The incubation mixture included 1 μg of poly (dI-dC) in a binding buffer (25 mM HEPES, pH 7.9, 0.5 mM EDTA, 0.5 mM DTT, 1% NP-40, 5% glycerol, 50 mM NaCl). The DNA/protein complex was electrophoresed on 4.5% nondenaturing polyacrylamide gels in 0.5×Tris/borate/EDTA buffer. (0.0445 M Tris, 0.0445 M. borate, 0.001 M EDTA). A double-stranded mutated oligonucleotide, 5'-AGTTGAGGCGACTTTCCCAGGC-3' (SEQ ID NO:2) was used to examine the specificity of binding of NF-kB to DNA (the underlined sequence is identical to kB consensus sequence except for a G-to-C substitution in the NF-kB/Rel DNA binding motif). The specificity of binding was also examined by competition with the unlabeled oligonucleotide.

Chemicals. L-Arginine, lipopolysaccharide (LPS), miconazol, tetrodotoxin (TTX), papaverine (PPV), tetraethylammonium, 4-aminopyridine, N-nitro-L-arginine (L-NNA), indomethacin, eicosatriynoic acid (ETI) and glipizide were obtained from Sigma Chemical Co. (St. Louis, Mo.). Iberiotoxin was obtained from RBI (Natick, Mass.) Oroxylin A was isolated from the root of *Scutellaria baicalensis* (Labiatae) (Chen et al., 1999). All drugs were dissolved in deionized water as stock solutions before experiments and added as final concentrations in the Kreb's solution or the incubation medium.

General procedure. Fresh heads of adult pigs of either sex were collected from local packing companies (Excel, Beardstown, Il, and Turasky's Y-T Packing, Springfield, Ill.). The entire brain, with dura matter attached, was removed and placed in Kreb's bicarbonate solution equilibrated with 95% $O_2$ and 5% $CO_2$ at room temperature. The composition of the Kreb's solution was as follows (mM): NaCl, 122.0; KCl, 5.16; $CaCl_2$, 1.2; $MgSO_4$, 1.22; $NaHCO_3$, 25.6; ethylenediamine tetraacetic acid, 0.03; L-ascorbic acid, 0.1; and glucose, 11.0 (pH 7.4). The circle of Willis (internal carotid and posterior communicating arteries) was dissected, and surrounding tissue was cleaned off under a dissecting microscope. Some cerebral arteries were mechanically denuded of endothelium before experiments. The successful removal of endothelial cells was verified by lack of L-Arginine-induced relaxation.

In vitro tissue bath studies. The arterial segment (4 mm long) of the circle of Willis was dissected and cannulated with a stainless-steel rod (30–28 gauge) of hemispherical section, and a short piece of platinum wire, and mounted horizontally in a plastic tissue bath containing 6 ml of Krebs' bicarbonate solution. The platinum wire was bent into a U shape and anchored to a gate. The stainless-steel rod was connected to a stain gauge transducer (UC3, available from Gould) for isometric recording of changes in force. The temperature of Krebs' solution in the tissue baths, equilibrated with 95% $O_2$ and 5% $CO_2$, was maintained at 37° C. Tissues were equilibrated in the Krebs' solution for an initial 30 minutes and were mechanically stretched to a resting tension of 0.75 g for another 30 minutes. The segments of the circle of Willis were precontracted with 9,11-dideoxy-9α,11α-epoxymethanoprostagladin $F_{2α}$(U-46619, 1 μM) to induce an active muscle tone of 0.5–0.75 g. Experimental drugs such as L-arginine and Oroxylin A of various concentrations, and TNS at 2,4,8 Hz were applied to induce relaxation. The arteries were then washed with pre-warmed Krebs' solution. A similar magnitude of active muscle tone again was induced with U-46619, and induction of relaxation by experimental drugs or TNS were repeated to compare with the relaxation before wash. For TNS, tissues were electrically, transmurally stimulated with a pair of electrodes through which 100 biphasic square-wave pulses of various frequencies were delivered. Stimulation parameters were continuously monitored on a Tektronix oscilloscope. The neurogenic origin of this TNS-induced response was verified by its complete blockade by TTX (0.3 μM) or L-NNA (30 μM). At the end of each experiment, papaverine (PPV, 300 μM) was added to induce a maximum relaxation. The magnitude of a vasodilator response induced by experimental drugs and TNS was expressed as a percentage of the maximum response induced by PPV.

Culture of smooth muscle cells. The entire brain with dura attached was removed and placed in ice-cold sterile phosphate-buffered saline (PBS) (140 mM NaCl, 4 mM KCl, 1 mM $KH_2PO_4$, pH 7.4) containing antibiotics (100 U/ml penicillin G potassium, 100 μg/ml streptomycin sulfate, and 0.25 μg/ml fungizone) (Fisher Scientific, Springfield, N.J.). The arteries of the circle of Willis were removed and cleaned of surrounding tissue under a dissecting microscope. The arteries were then placed on a sterile petri dish and sliced longitudinally. The luminal surface was rubbed with a sterile cotton swab to remove endothelial cells. The vessels were placed in DMEM (Dulbecco's Modified Eagle Medium, Life Technologies, Grand Island, N.Y.) containing antibiotics and stored overnight at 4° C. The vessels were cut into approximately 2×2-mm explants, placed in a 10 cm petri dish, covered with DMEM containing antibiotics plus 20% FBS (fetal bovine serum, Sigma Chemical Co., St Louis, Mo.), and placed in an incubator in an atmosphere of 5% $CO_2$ in air at 37° C. After 7–10 days, the cells were removed and the medium was changed every 2–3 days until the cells reach confluence. Cells were then passaged into 24-well culture dishes using 0.25% trypsin and were grown in DMEM plus 10% fetal bovine serum (FBS, available from Hyclone Lab of Logem, Utah) and antibiotics. Experiments were performed on cells at passages 2–10.

Incubation of cerebral arteries with LPS. Endothelium-denuded arterial segments of the circle of Willis were incubated for 20 hours (37° C.) in M199 medium containing 5% fetal bovine serum (Life Technologies, Grand Island, N.Y.) in the presence of LPS (10 μg/ml) with or without oroxylin A. Additional segments of arteries were incubated in the same medium in the absence of LPS for same length of time, and served as negative controls.

Western blots. Total cellular extract of smooth muscle cells was prepared and separated on 7.5% sodium dodecyl sulfate-polyacrylamide minigels (Hoefer Pharmacia Biotech, San Francisco, Calif.) and transferred to immobilon polyvinylidene difluoride membranes (Millipore, Bedford, Mass.). The membrane was incubated overnight at 4° C. with 1% bovine serum albumin and then incubated with anti-iNOS monoclonal antibody (Transduction Laboratories, Lexington, Ky.). Expression of iNOS was detected by NBT and BCIP staining (Sigma Chemical Co., St. Louis, Mo.).

Immunohistochemistry. For demonstrating the expression of iNOS protein induced by LPS in porcine cerebral arteries and smooth muscle cells, immunohistochemistry was carried out using an indirect immunofluorescence method. The arteries of the circle of Willis were incubated in the presence of LPS with or without oroxylin A at 37° C. for 20 hours, and followed by fixation with PPPFL fixative (periodate-picric acid-paraformaldehyde-lysine) for 24 hours. After fixation, arteries were rinsed in 0.01 M PBS (pH 7.4) 3 times and sectioned at 12 μm thickness with a Micron 505E cryostat microtome (Zeiss, N.Y, N.Y.). The sections were mounted on coated slides (Vectabond Reagent; Vector Labs) and processed for immunohistochemistry. Avidin-biotin complex indirect immunohistochemical methods (Vector Labs) were used to demonstrate iNOS immunoreactivity with fluorescein isothiocyanate (FITC) as chromogen. Briefly, the sectioned arteries were incubated in 0.5% normal goat serum with avidine D solution (Avidin/Biotin Blocking Kit; Vector Labs) to block endogenous biotin and then incubated with primary antibody against iNOS at a dilution 1:250 for 4 hours at room temperature. After three washes in 0.01 M PBS (pH 8.2), samples were incubated with biotinated affinity purified goat anti-mouse IgG (1:200 dilution) (Vectastain ABC Kit; Vector Labs) for 30–60 minutes at room temperature followed by 0.01 M PBS (pH 8.2) washes for three times, and then incubated with FITC-labeled avidin D (Fluorescein avidin D; Vector Labs) for 60 minutes at room temperature.

Photomicrographs of immunofluorescence at 20× were immediately taken with an Olympus fluorescence microscope fitted with an FITC filter. Similar immunostaining method was used for the cultured primary smooth muscle cells except that the cultured cells growing on poly-D-lysine coated glass coverslip were fixed in cold methanol for 20 minutes and rinsed three times with PBS.

Statistical analysis. Results were expressed as means±S.E.M. Statistical analysis was evaluated by student's t test for paired samples as appropriate. The $P<0.05$ level of probability was accepted as significant.

EXAMPLE 1

Effects of two flavonoids (myristricin isolated from Cuphea hyssopifolia and oroxylin A isolated from Scutellaria baicalensis), four ellagitannins (penta-O-galloyl-β-glucopyranose, woodfordin C. oenothein B, cuphiin D1; all were isolated from C. hyssopifolia) and two anthraquinones (emodin and physcion; both were extracted from Rheu palmatum) on PLS-induced NO production and expression of iNOS and COX-2 in RAW264.7 macrophages were studied, according to the procedures described above. The data indicated that oroxylin A was most potent among the compounds tested in blocking LPS-induced iNOS and COX-2 gene expression. The blocking effect of oroxylin A occurred via inhibition of binding of transcription factor NF-kB to iNOS promoter. Emodin which also showed a potent inhibitory effect, comparable to oroxylin A, on LPS-induced iNOS gene expressions. Similar findings were found in Bcl-2 overexpressed RAW264.7 cells.

The effects of flavonoids, ellagitannins, anthraquinones on LPS-induced NO production in macrophages were studied as follows. The chemical structures of two flavonoids (myricitrin, N1; oroxylin A, N2) four ellagitannins (penta-O-galloyl-β-glucopyranose, N3; woodfordin C, N4; onothein B, N5; cuphiin, N6), and two anthraquinones (emodin, N7; physcion, N8) that were used in the present study were shown in FIG. 1. The effects of these eight compounds on NO production in RAW264.7 macrophages were investigated. The accumulated nitrite in the culture medium was used as an index for NO synthesis from these cells. Each of these eight compounds, at the concentration of 20 μg/ml, did not interfere with the reaction between nitrite and Griess reagent. Unstimulated macrophages, after 24 hours of incubation in the culture, produced background levels of nitrite (Control, FIG. 2). When the resting cells were incubated with each indicated compound alone, amount of nitrite in the medium was maintained at a background level similar to that in the unstimulated samples. After treatment with LPS (100 ng/ml) for 24 hours, nitrite concentration was significantly increased for about 20 fold (~35 μM). When macrophages were incubated with various concentrations of each compound (5, 10 or 20 μg/ml) (1, 2 or 3 respectively, FIG. 2) together with 100 ng/ml LPS for 24 hours, significant inhibition of nitrite production was detected in the presence of oroxylin A (N2) and emodin (N7), in a concentration-dependent manner. The remaining compounds only at highest concentration (20 μg/ml) showed slight inhibition on LPS-induced nitrite production (FIG. 2). Examination of effects of these eight compounds at 20 μ/ml on RAV264.7 cell viability by MTT assay indicated that only emodin at this high concentration caused a slight cytotoxity (~30%), while other compounds did not affect the cell viability.

EXAMPLE 2

Figure 3:
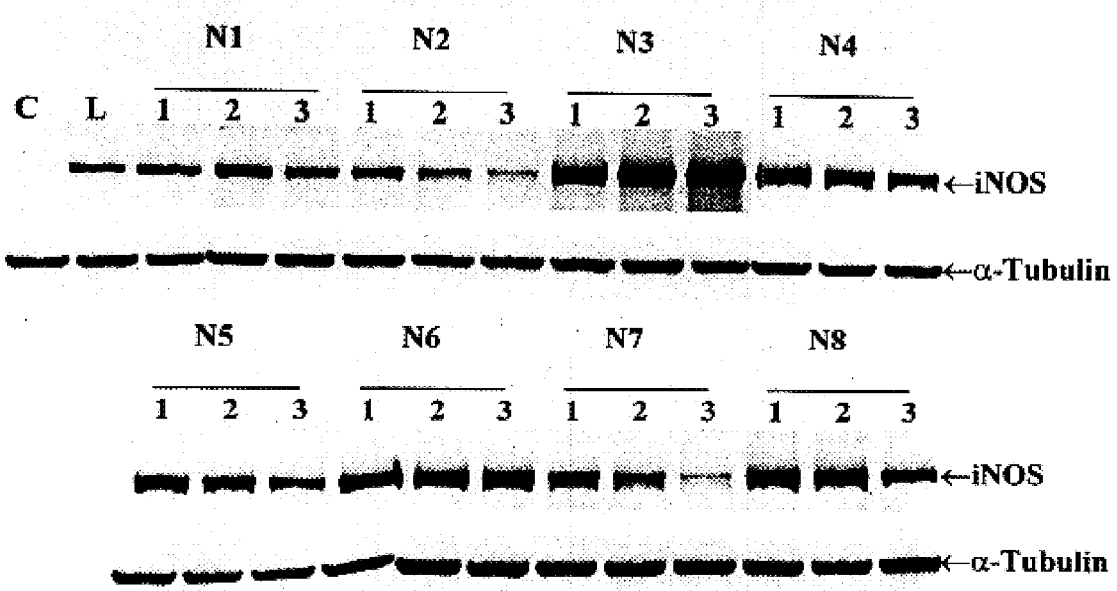
FIG. 3 shows the inhibition of LPS-induced iNOS proteins in RAW264.7 macrophages by various concentrations of FIG. 1 compounds.
Figure 4:
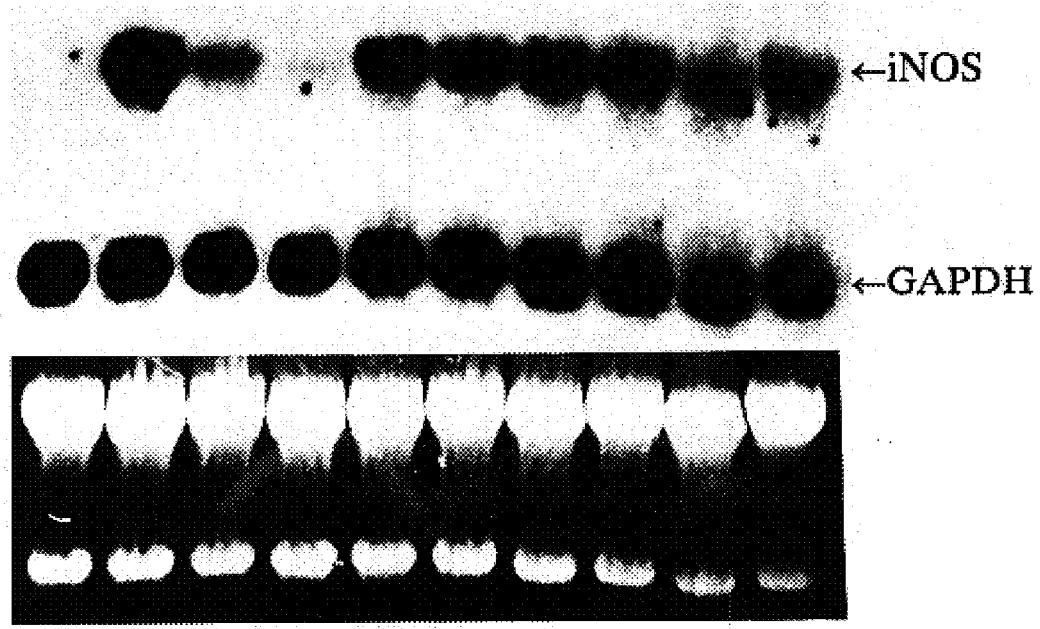
FIG. 4 shows the effects of various FIG. 1 polyphenols on LPS-induced iNOS mRNA in RAW264.7 macrophages.

RAW264.7 macrophages did not express detectable levels of iNOS protein (FIG. 3, C) or iNOS mRNA (FIG. 4, C) when incubated with medium alone for 24 or 7 hours, respectively. Basal level of iNOS in RAW264.7 cells was not affected when incubated with each of the indicated eight compounds alone, while 100 ng/ml LPS induced a dramatic increase in iNOS protein (FIG. 3, L) and mRNA (FIG. 4, L) in these cells. Examination of effect of each of these-eight compounds on LPS-induced iNOS protein and mRNA demonstrated that among these eight compounds, only oroxylin A (N2) and emodin (N7) inhibited LPS-induced iNOS protein in a concentration-dependent manner, while amount of α-tublin protein as an internal control remained unchanged, as shown in FIG. 3. The effect of these compounds in inhibiting LPS-induced iNOS mRNA is demonstrated in FIG. 4.

Figure 5A:
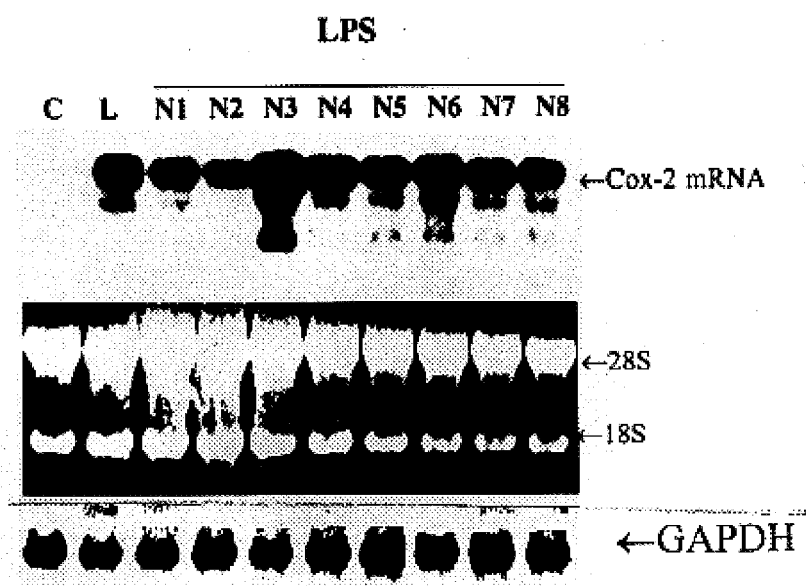
FIG. 5 shows the effects of various FIG. 1 polyphenols on expression of COX-2 mRNA and protein in RAW264.7 macrophages.
Figure 5B:
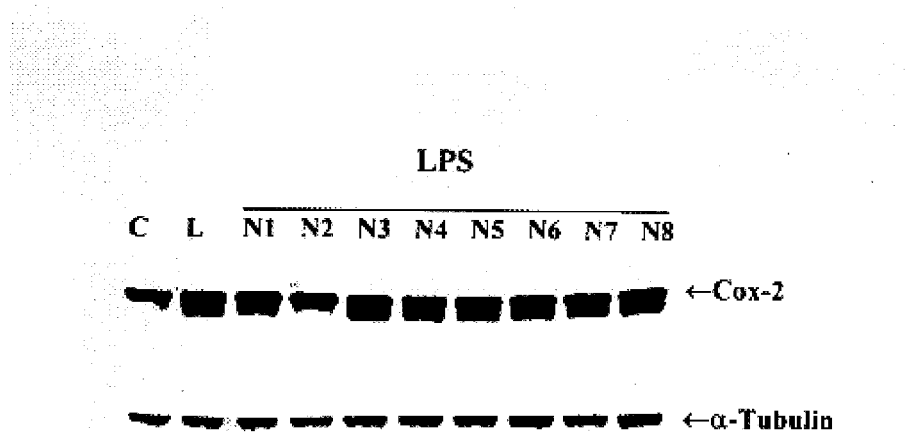
Figure 5C:
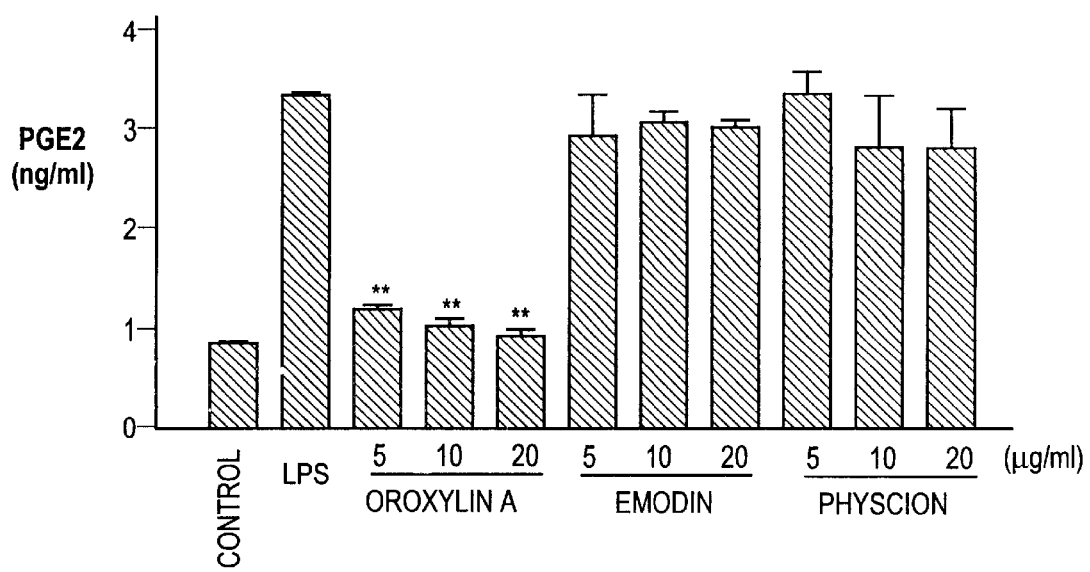

Since NO may directly activate expression of COX isoforms, and induction of COX gene expression has been shown to be involved in process of LPS-mediated response (Cao, C. et al., Brain Res., 697, 187–196, 1995), the effect of these eight compounds on LPS-induced COX-2 gene expression was also investigated. The results indicated that only oroxylin A inhibited LPS-induced COX-2 gene expression in both protein and mRNA levels (FIG. 5).

Example 3

Figure 6:
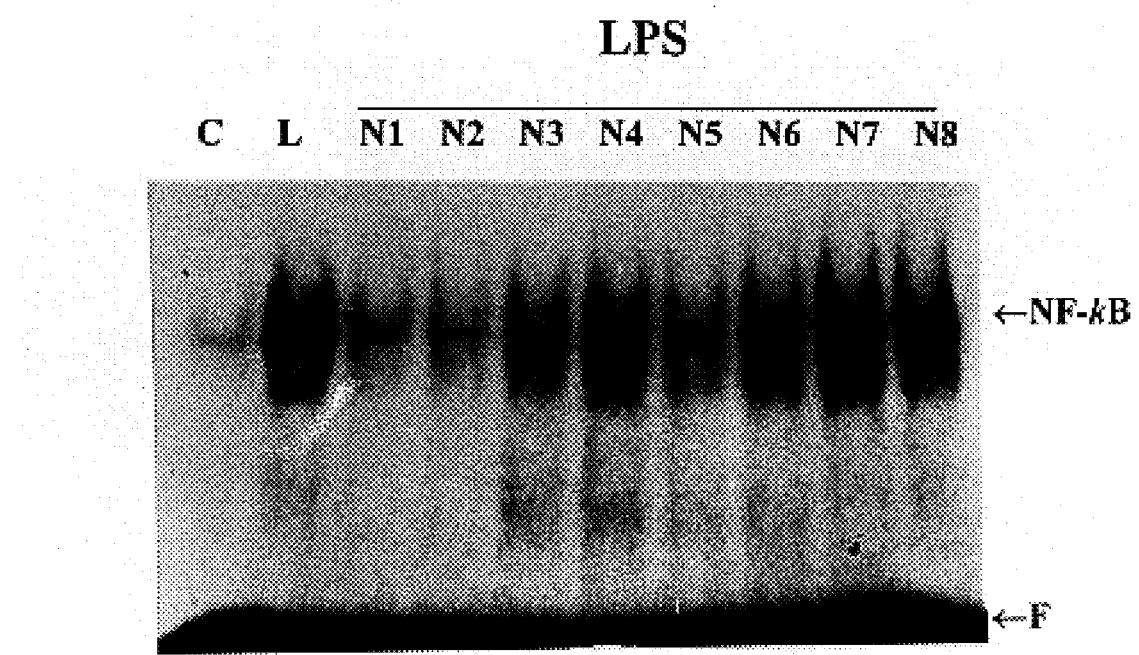
FIG. 6 shows the effects of various FIG. 1 polyphenols on LPS-induced NF-kB binding in RAW264.7 macrophages.
Figure 6:
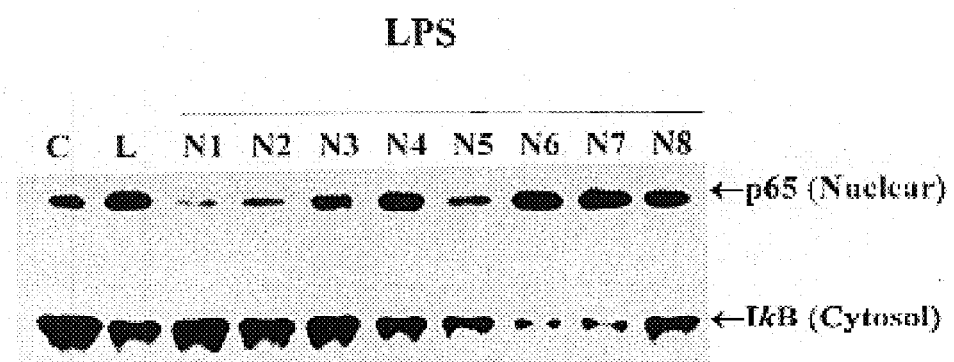

NF-kB is a transcription factor that is activated in response to stimulation by LPS, and activation of NF-kB is an essential factor in inducing iNOS gene expression in macrophages (Kim, Y. M., Biochem. Biophys. Res. Commun. 236, 655–660, 1997). To assess the effect of these compounds (20 μg/ml) on early stage of iNOS gene expression, the activation of NF-kB in RAW264.7 macrophages was examined using the electrophoretic mobility shift assay (EMSA) (FIGS. 6i and 6ii). One hour after activation with LPS, the binding of NF-kB was increased remarkably in nuclear extracts of macrophages. This inductive NF-kB binding activity was significantly inhibited by myricitrin, oroxylin A and oenothein B (FIG. 6). In contrast, emodin did not affect the activation of NF-kB by LPS, although it was shown to inhibit nitrite production and iNOS gene expression. The NF-kB complex formation was specifically blocked by the addition of a molar excess of specific unlabeled consensus oligomer, but was not inhibited by the mutated unlabeled oligomer. In order to further demonstrate that inhibition of NF-kB activation by oroxylin A, a Luc-reporter plasmid containing five NF-kB binding sites in the enhancer element was transiently transfected into RAW264.7 cells, and analysis of luciferase activity was performed to identify the levels of NF-kB activation. The results showed that oroxylin A efficiently decreased the LPS-induced luciferase activity by four fold (FIG. 6iii). These data were consistent with the results of analyzing NF-kB binding by EMSA. The heteromeric NF-kB complex is sequestered in the cytoplasm as an inactive precursor complexed with an inhibitory protein, an IkB-like protein and LPS induced NF-kB activation through increasing nuclear p65 protein associated with a decrease of cytosolic IkB protein. By western blot analysis, incubation of RAW264.7 macrophages with 100 ng/ml LPS for 30 minutes was able to increase of NF-kB (p65) in the nuclear fraction and decrease of IkB protein in the cytosol (FIG. 6iv). This phenomenon was significantly inhibited by 20 μg/ml myristricin (N1), oroxylin A (N2) and oenothein B (N5) (FIG. 6iii). Emodin (N7) and cuphiin D1 (N6) treatment did not block the increase of p65 in the nucleus or degradation of IkB induced by LPS.

EXAMPLE 4

Figure 7A:
FIG. 7 shows the detection of iNOS protein and nitrite production in LPS-treated parental RAW264.7 overexpressed RAW264.7 cells.
Figure 8:
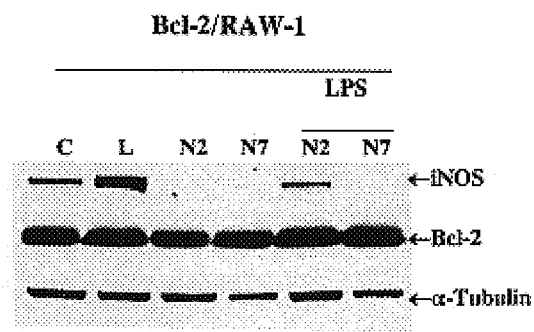
FIG. 8 shows the effects of oroxylin A and emodin on LPS-induced iNOS protein and nitrite production in Bcl-2/RAW-1 and Bcl-2/RAW-2 cells.
Figure 8:
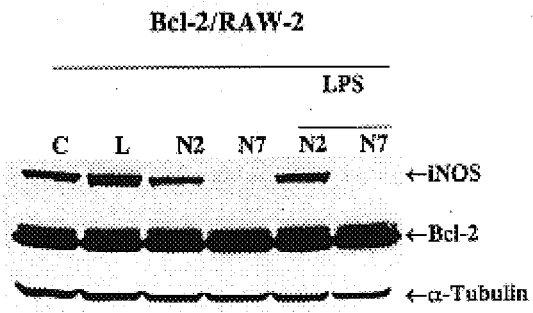
Figure 9A:
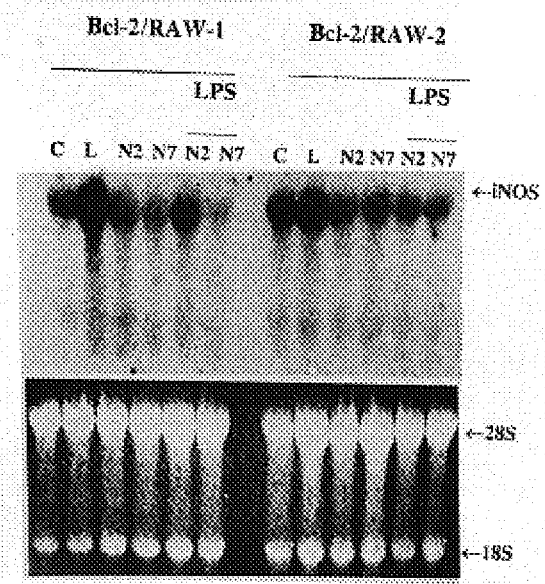
FIG. 9 shows the effects of oroxylin A and emodin on LPS-induced iNOS and. COX-2 mRNA in Bcl-2-overexpressed RAW264.7 cells.
Figure 9B:
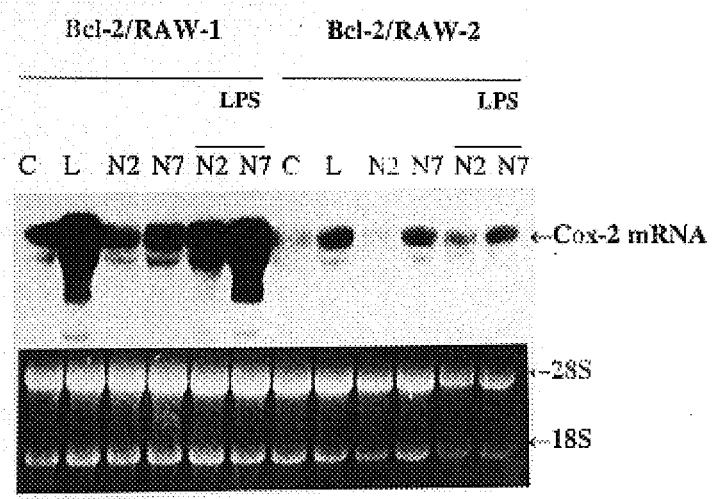

RAW264.7 macrophages were transfected with the plant pC-Δj-bcl-2 also carrying a neomycin resistance gene. Stable Bcl-2 protein expression was assessed by western blot analysis with an anti-human Bcl-2 specific antibody. Two dependent clones termed Bcl2/RAW-1 and Bcl 1/RAW-2 showed the substantial Bcl-2 overexpression (FIG. 7A). Both clones expressed higher levels of Bcl-2 protein and neomycin-vector transfected RAW264.7 (neo/RAW) lack any human Bcl-2 protein in cells. The endogenous iNOS protein in Bcl2RAW-1 and Bcl-2/RAW-2 cells is higher than that in neo/RAW cells, and the levels of iNOS protein is Bcl-2/RAW-2>Bcl-2/RAW-1>neo/RAW. Upon treatment with 100 ng/ml LPS, significant induction of iNOS protein and nitrite production was detected in Bcl2/RAW-1 and neo/RAW, however Bcl-2/RAW-2 cells were less sensitive to LPS treatment (FIG. 7B). In order to examine whether oroxylin A and emodin inhibit LPS-induced iNOS and COX-2 gene expressions in Bcl-2-overexpressed RAW264.7 cells, both Bcl-2/RAW-1 and Bcl-2/RAW-2 were incubated with oroxylin A or emodin (20 μg/ml) followed by activation with LPS (100 ng/ml). Analysis of iNOS and COX-2 gene expression was then performed by northern and western blots. Oroxylin A (N2) or emodin (N7) treatment inhibited LPS-induced nitrite production and iNOS gene expressions in both Bcl-2-transfected cells (FIGS. 8 and 9A). Upon analysis of COX-2 mRNA, oroxylin A but not emodin inhibited LPS-induced COX-2 mRNA in Bcl-2-overexpressed RAW264.7 macrophages (FIG. 9B). These results were in accordance with the results derived from parental RAW264.7 macrophages.

EXAMPLE 5

Figure 10A:
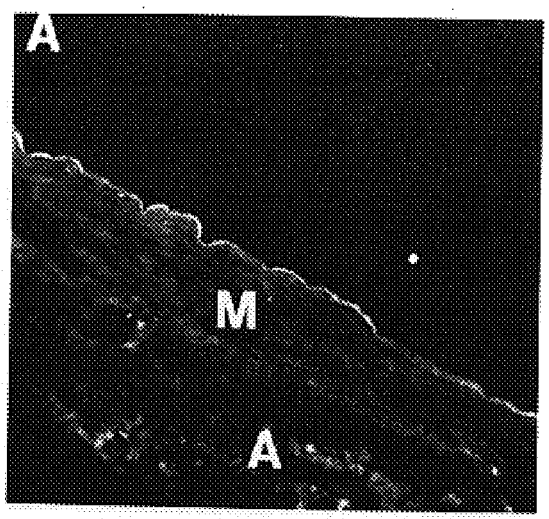
FIG. 10 is a photomicrograph on 50 μm scale showing iNOS-immunoreactivities in Muscle (M) of background level in porcine cerebral arteries of control samples incubated in medium only (A), of significance expressed in porcine cerebral arteries incubated in medium containing LPS (10 μg/ml) (B) and of background level in porcine cerebral arteries incubated in the presence of LPS and oroxylin A (C). (A=adventitia)
Figure 10B:
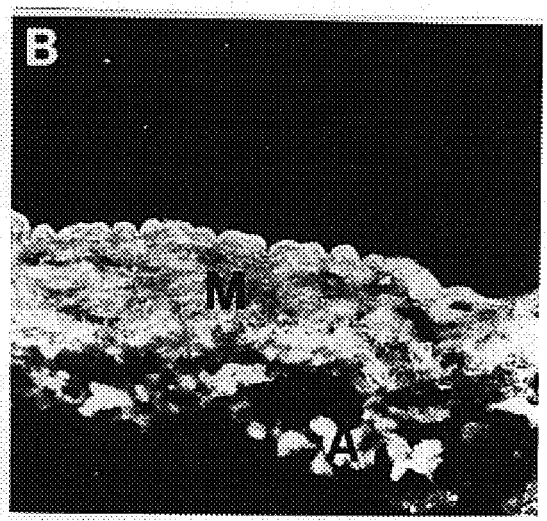
Figure 10C:
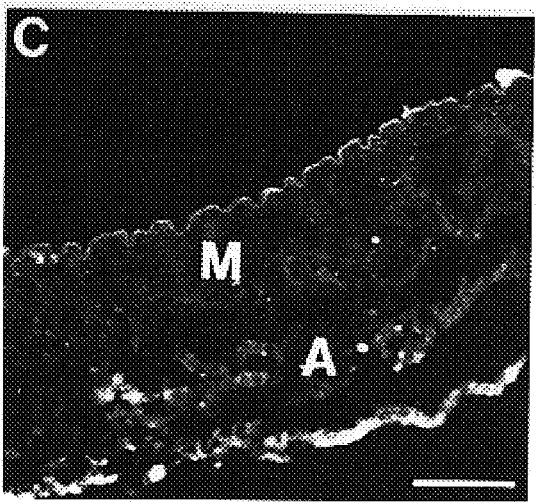

Results from immunohistochemical studies demonstrated that iNOS-immunoreactivities, which were occasionally found in the adventitia, were never found in the medial smooth muscle layer (FIG. 10A, n=6). The iNOS-immunoreactivities, however, were significantly expressed in the medial smooth muscle layer in arteries following incubation with LPS (10 μg/ml) for 20 hours (FIG. 10B, n=6). The LPS-induced expression of iNOS in the muscle layer was not found in arteries following concomitant incubation with oroxylin A (60 μM) (FIG. 10C, n=6).

Figure 11:
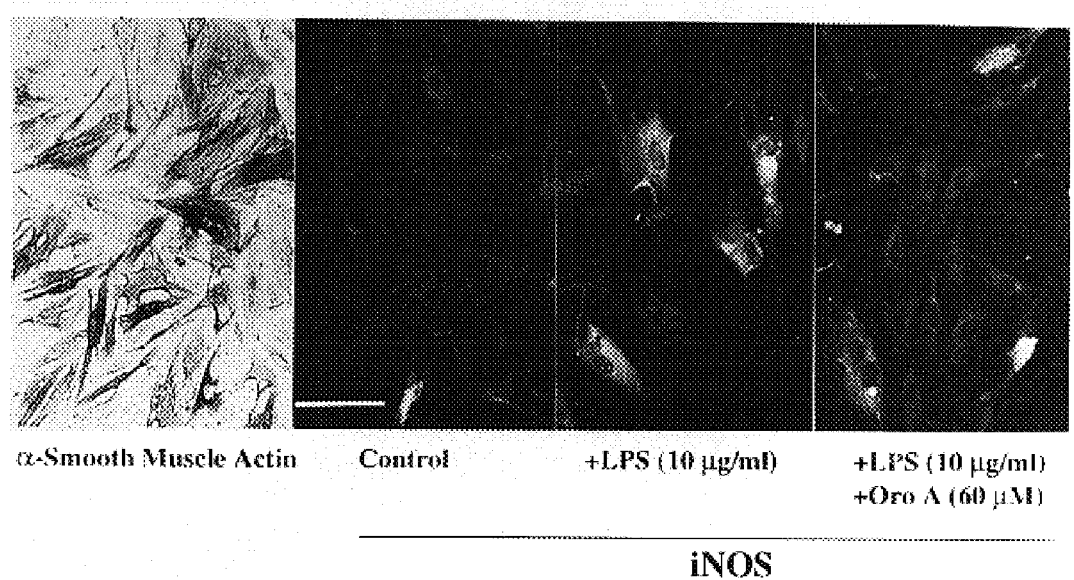
FIG. 11 is a photomicrograph on 50 μm scale showing oroxylin A inhibition of LPS-induced expression of iNOS proteins in cultured primary smooth muscle cells from porcine cerebral arteries.
Figure 12:
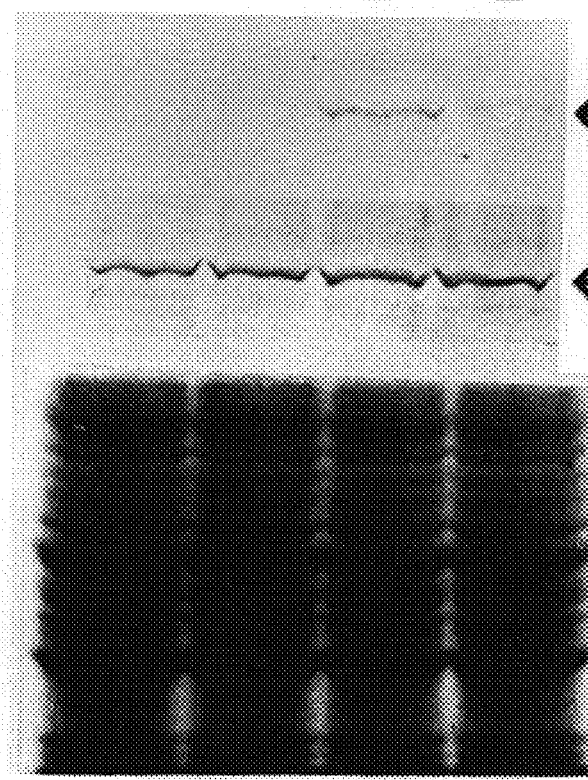
FIG. 12 is a Western blot analysis showing the effect of oroxylin A on iNOS expression in cultured primary smooth muscle cells isolated from porcine cerebral arteries of the circle of Willis. Cells incubated in the medium alone (lane 1) expressed some trace of iNOS proteins. Incubation in the presence of LPS (10 μg/ml) (lane 2) significantly increased iNOS proteins. The expression of iNOS proteins was decreased by oroxylin A (30 μM in lane 3, and 60 μM in lane 4) in a concentration-dependent manner. Oroxylin A at the concentrations used did not affect the expression of nNOS in each group. The total loading proteins expressed by commasie blue stain were not different among different experimental groups.

The LPS induction of iNOS and its inhibition by oroxylin A in porcine cerebral arterial smooth muscle cells was further demonstrated in the primary culture of smooth muscle cells isolated from these arteries (FIG. 11). The smooth muscle nature of the cultured cells was verified by the presence of over 95% of cultured cells which were immunoreactive for smooth muscle α-actin (FIG. 11). After incubation in the presence LPS (10 μg/ml) for 20 hours, most cultured cells were iNOS-immunoreactive (iNOS-I). The iNOS-I cells were drastically decreased when these cells were cultured concomitantly with oroxylin A (60 μM). This was further verified by the results from Western blot analysis that LPS incubation alone significantly increase iNOS proteins in the cultured smooth muscle cells (FIG. 12). The expression of iNOS proteins was decreased by oroxylin A in a concentration-dependent manner. Oroxylin A at the concentrations used did not affect the expression of nNOS, while the total loading proteins were not different among different experimental groups.

EXAMPLE 6

Figure 13A:
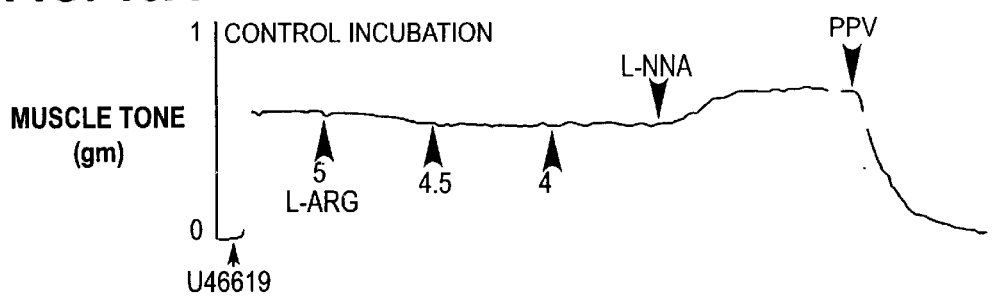
FIG. 13 shows effects of oroxylin A on L-arginine-induced relaxation in cerebral arteries without endothelial cells in the presence of active muscle tone induced by U-46619. Numbers with arrowheads indicate negative log molar concentration of L-arginine (L-Arg).
Figure 13B:
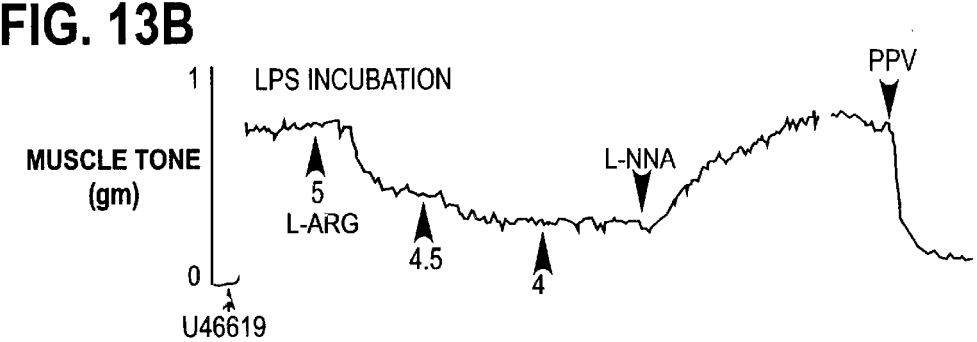
Figure 13C:
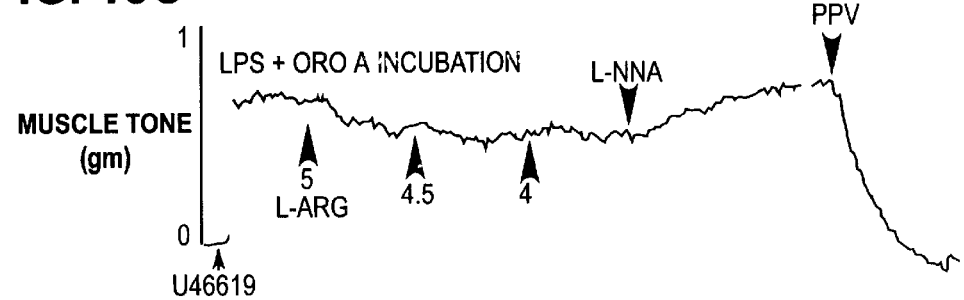
Figure 13D:
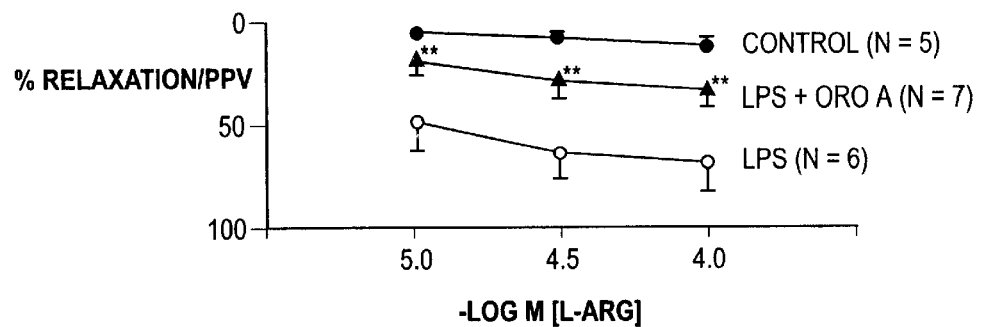

L-Arginine (10–100 μM) did not induce relaxation in fresh cerebral arterial rings without endothelial cells or induced very small relaxation in those incubated in culture medium for 20 hours (FIGS. 13A and 13D). However, after incubation with LPS (10 μg/ml) for 20 hours, these arterial rings without endothelial cells in the presence of U-46619 (1 μM)-induced active muscle tone significantly relaxed upon application of L-Arginine (FIGS. 13B and 13D). This LPS-rendered L-Arginine-induced relaxation was significantly decreased when the arteries without endothelial cells were incubated concomitantly with oroxylin A (60 μM) (FIGS.

13C and 13D). L-NNA (30 μM) given at the end of each experiment increased basal tone significantly greater in arterial rings incubated with LPS alone than the control arteries and arteries co-incubated with LPS and oroxylin A.

EXAMPLE 7

Figure 14A:
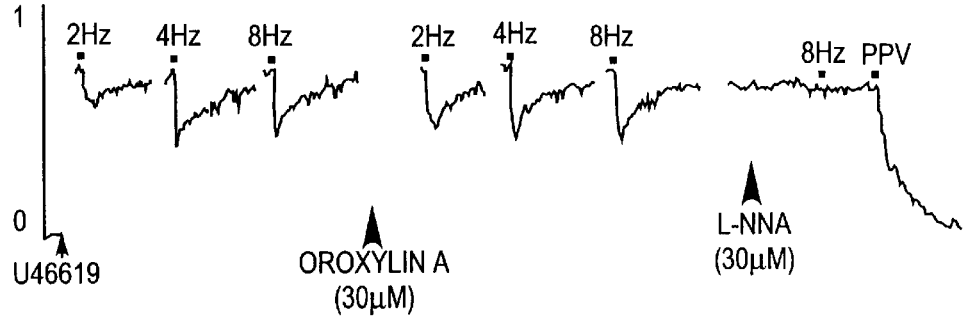
FIG. 14A shows a representative tracing showing relaxation of a cerebral arterial ring without endothelium elicited by electrical stimulation of cerebral perivascular nerves. The increased neurogenic vasodilation by oroxylin A is summarized in FIG. 14B.
Figure 14B:
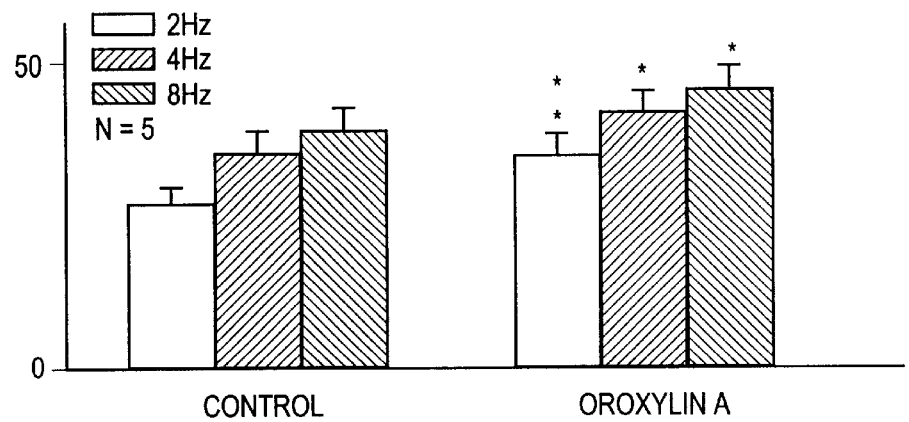
Figure 15A:
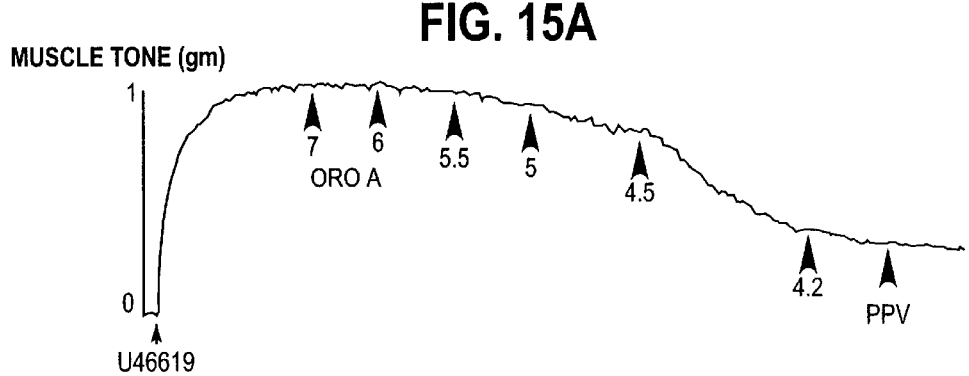
FIG. 15 shows a representative tracing illustrating concentration-dependant inhibition by oroxylin A of 9,11-dideoxy-9α,11α-epoxymethano-prostagladin $F_{2\alpha}$(U-46619)-induced active muscle tone in a porcine cerebral artery without endothelial cells (A). In the presence of active muscle tone induced by KCl (80 mM), oroxylin A (oro A) (1–60 μM) however failed to induce sustained relaxation (B). Numbers with arrowheads indicate negative molar concentrations of oroxylin A. PPV=papaverine, 300 μM.
Figure 15B:
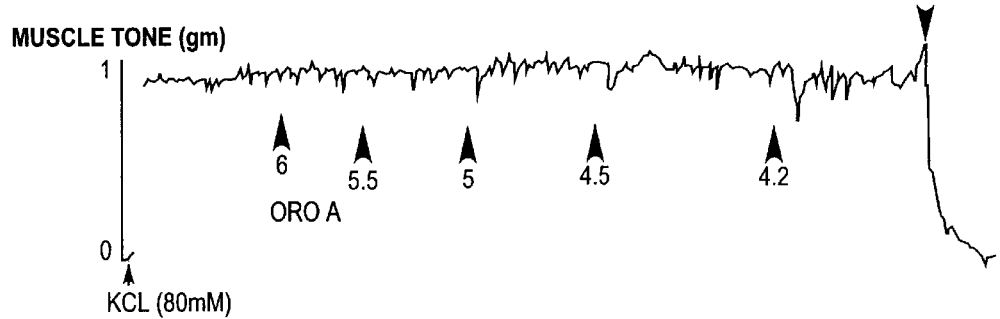

Consistent with the previous findings that transmural nerve stimulation (TNS) at various frequencies elicited relaxation in cerebral arterial segments with or without endothelial cells in the presence of active muscle tone induced by U-46619 (1–3 μM) (FIG. 14). The relaxation elicited by TNS at 2, 4, and 8 Hz, which was tetrodotoxin (TTX, 0.3 μM)-sensitive, was not inhibited but was slightly and significantly enhanced by acute administration of oroxylin A (30 μM) (FIG. 15B). The residual relaxation was abolished by L-NNA (30 μM).

EXAMPLE 8

Figure 16A:
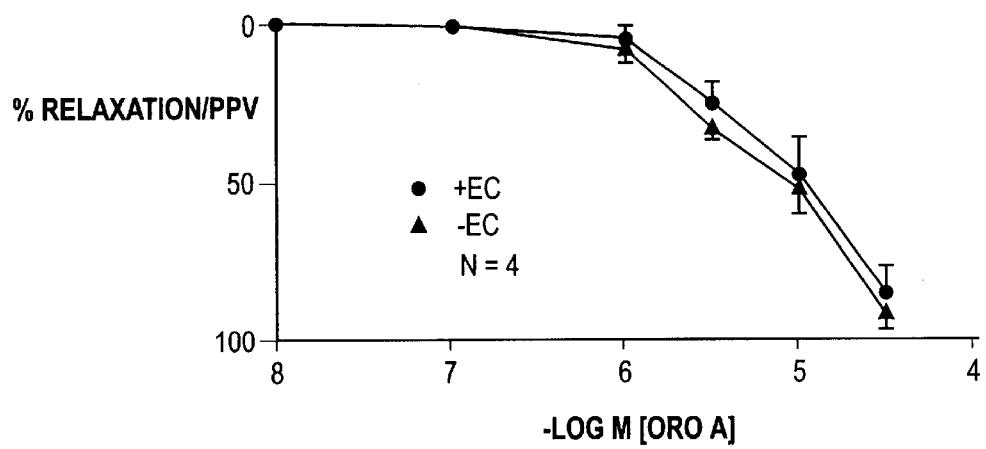
FIG. 16 shows a decrease in muscle tone induced by oroxylin A. Oroxylin A in a concentration-dependent manner decreased U-46619 (1 μM)-induced active tone in porcine cerebral arteries with (+EC) and without (–EC) endothelium (FIG. 16A). The decrease in muscle tone induced by oroxylin A was not different (p>0.05) between the arteries with and those without endothelium. Two reproducible concentration-relaxant response relationships were determined on consecutive applications of oroxylin A (0.1 μM–30 μM) in the same arteries with 60 minute intervals and 3 washes between two applications. There was no significant difference (p>0.05) between the two responses. Relaxation was estimated as a percentage of maximum relaxation induced by papaverine (PPV) (300 μM). Values are means±S.E.M.; n is the number of experiments.
Figure 16B:
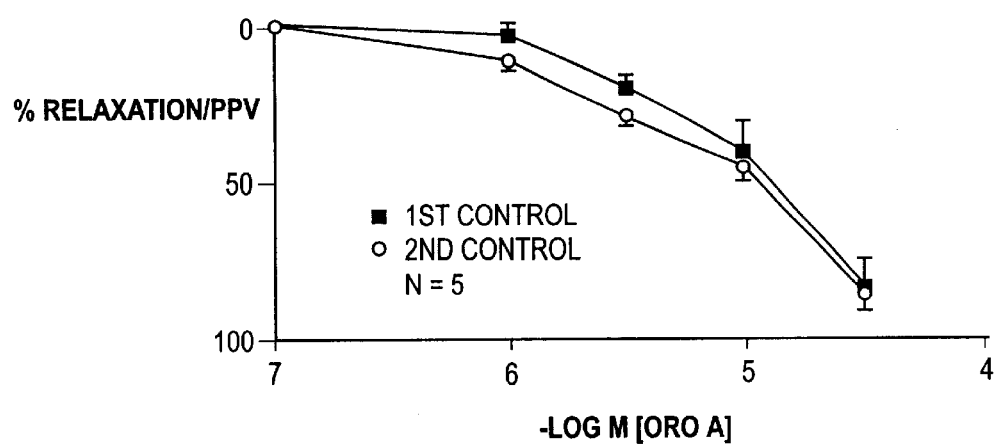

Arterial ring segments of the circle of Willis with intact endothelium pre-contracted with U-46619 (1 μM) relaxed upon application of oroxylin A (0.1–30 μM) in a concentration-dependent manner with the maximum relaxation achieved at 30 μM (FIG. 16A, B). The medium effective concentration ($EC_{50}$) was 7.9(4.6–13.8 μM) (n=4). DMSO, a dissolving medium for oroxylin A, at the concentration used (as much as 0.1% vol/vol) had no effects on basal tone. Oroxylin A-induced sustained relaxation was not different (p>0.05) from that in endothelium-denuded arteries with $EC_{50}$=8.4(5.8–9.8) μM (n=12) (FIG. 16A). Two consecutive oroxylin A full concentration-response curves performed in same arterial preparations with 60 minute intervals and 3 washes between two applications were not different (p>0.05, n=5, FIG. 16B). Effects of experimental drugs on oroxylin A-induced relaxation were therefore examined by applying the experimental drugs to the tissues prior to the commencement of the second concentration-response curves. In parallel, other polyphenolic compounds such as epigallocatechin gallate, emodin, ginkgolide A and ginkgolide B at concentrations as high as 100 μM caused very small relaxation or no response (n=4 for each compound) (data not shown).

EXAMPLE 9

When basilar arterial rings precontracted with 80 mM KCl, oroxylin A did not induce sustained relaxation in cerebral arteries with or without endothelial cells (FIG. 15B). Oroxylin A induced only small transient relaxation (FIG. 15B). The transient relaxation induced by maximum concentration of oroxylin A (60 μM) in KCl-pre-contracted arterial rings (20.2±1.63% of PPV-induced maximum relaxation, n=5) was significantly smaller than that found in same arteries with similar active muscle tone contracted with U-46619 (95.1±4.31% of PPV-induced maximum relaxation, n=5) (FIG. 15A).

EXAMPLE 10

Figure 17A:
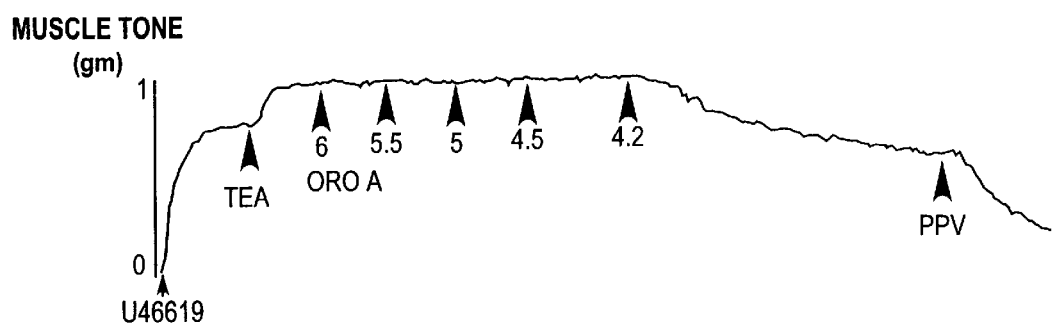
FIG. 17 shows a representative tracing illustrating that TEA, which further raised the basal tone, blocked the relaxation induced by oroxylin A in a cerebral arterial ring without endothelial cells.
Figure 17B:
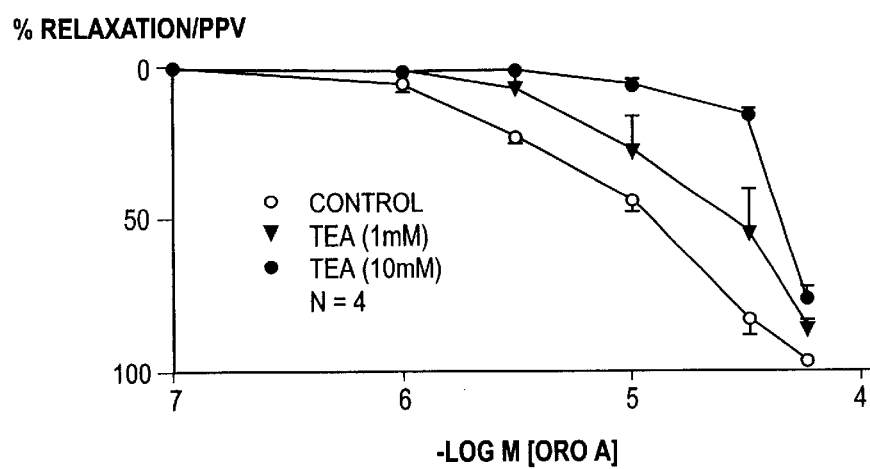

TEA, (tetraethylammonium) a nonspecific $K^+$ channels blocker, concentration-dependently (1–10 mM) inhibited oroxylin A-induced relaxation in cerebral arteries without endothelial cells (FIGS. 17A and 17B and Table 1). TEA at 1 mM significantly shifted the oroxylin A concentration response curves to the right (FIG. 17B and Table 1). TEA at 10 mM almost abolished relaxation induced by oroxylin A at concentrations lower than 30 μM. Relaxation induced by oroxylin A at 5.8 μM, however, was not significantly affected by TEA at this concentration (FIG. 17B). 4-aminopyridine (4-AP), a second nonspecific $K^+$ channel blocker, also significantly inhibited the vasodilatory effect of oroxylin A in arteries without endothelial cells pre-contracted with U-46619 (FIG. 18 and Table 1). Iberiotoxin (IBT, 100 nM), a preferential $Ca^{2+}$ activated potassium channel blocker, slightly but significantly inhibited oroxylin A-induced relaxation (Table 1). In contrast, glipizide (GLP, 30 μM), which is an ATP-sensitive $K^+$ channel blocker, did not affect oroxylin A-induced relaxation (FIG. 18 and Table 1).

TABLE 1

Effects of potassium channel inhibitors, lipoxygenase, NOS and cyclooxygenase inhibitors on oroxylin A-induced vasorelaxation in porcine cerebral arteries.

| Treatments | Oroxylin A (3 μM) | Oroxylin A (10 μM) | Oroxylin A (30 μM) | $EC_{50}$ (μM) |
|---|---|---|---|---|
| PPV Control (300 μM) | 24.6 ± 1.9 | 49.0 ± 3.4 | 86.0 ± 2.6 | 8.4(5.8–9.8) |
| TEA (1 mM) | 7.1 ± 3.0* | 31.5 ± 6.6 | 58.6 ± 6.7* | 21.5(7.4–51.3)* |
| TEA (10 mM) | 0** | 4.87 ± 1.5** | 16.3 ± 2.0** | 39.3(35.5–40.7)** |
| 4-AP (10 mM) | 1.8 ± 1.6** | 9.7 ± 2.0** | 28.4 ± 6.7** | — |
| IBT (100 nM) | 16.8 ± 3.1 | 30.8 ± 5.2** | 68.1 ± 7.2** | 15.0(11.2–19.5)* |
| ETI (10 μM) | 21.4 ± 2.1 | 41.3 ± 4.4 | 91.4 ± 1.5 | 8.1(3.8–13.8) |
| GLP (30 μM) | 24.6 ± 3.4 | 46.5 ± 7.1 | 84.2 ± 7.1 | 11.2(8.5–14.1) |
| MCN (5 μM) | 21.2 ± 3.4 | 37.4 ± 4.5 | 87.2 ± 2.6 | 10.5(7.4–14.1) |
| INDO (30 μM) | 23.0 ± 1.8 | 41.8 ± 5.6 | 89.1 ± 3.6 | 10.0(6.8–13.8) |
| L-NNA (60 μM) | 26.9 ± 3.4 | 45.3 ± 6.0 | 91.9 ± 2.8 | 11.4(8.5–14.8) |

Tetraethylammonium (TEA), glipizide (GLP), 4-aminopyridine (4-AP), miconazole (MCN), indomethacin (INDO), N-nitro-L-arginine (L-NNA) or iberiotoxin (IBT) was administered for 20 minutes before application of oroxylin A. Relaxation-induced by oroxylin A was estimated as a percentage of maximum relaxation induced by papaverine (PPV, 300 μM).
Values are means ± S.E.M.;
Control, n = 12;
Each experimental drug, n = 5;
*P < 0.05 and **P < 0.01, indicate significant differences from the control.
"—" = not measured.

EXAMPLE 11

The possibility that vasodilation induced by oroxylin A may be mediated by metabolites of the arachidonic acid cascade was examined. Oroxylin A-induced relaxation in cerebral arteries without endothelial cells was not affected by eicosatriyonic acid (ETI, an inhibitor of 5-, 12- and 15-lipoxygenase activity; 10 μM, n=5), miconazole (MCN, a competitive inhibitor of cytochrome P-450 epoxygenase; 5 μM, n=5) or indomethacin (INDO, an inhibitor of cyclooxygenase activity; 30 μM, n=5). Oroxylin A-induced relaxation was not affected by L-NNA (60–240 μM, n=5) either (FIG. 18 and Table 1). These results indicated that lipoxygenase metabolites and NO pathway were not involved in the vasodilator response induced by oroxylin A.

EXAMPLE 12

Figure 19A:
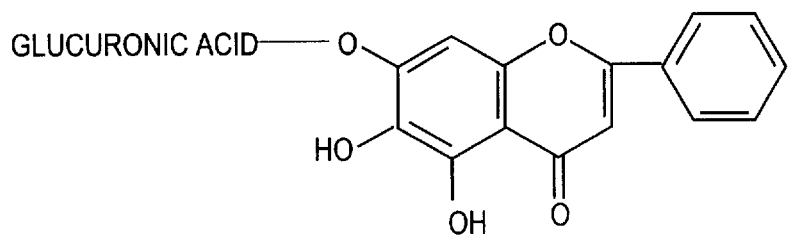
FIG. 19 shows the chemical structures of baicalin, baicalein and wogonin.
Figure 19B:
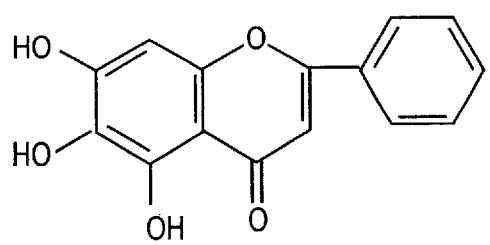
Figure 19C:
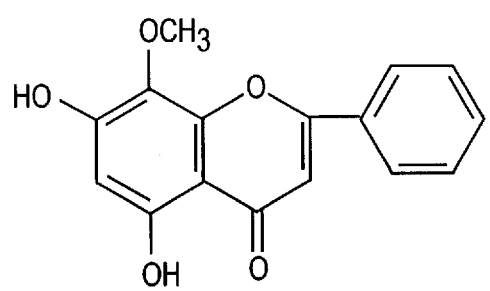

In the present study, three oroxylin A structurally related polyphenols isolated from Chinese herbs Huang Qui including baicalin, baicalein and wogonin (FIG. 19) were examined for their effects on LPS-induced nitric oxide (NO) production, iNOS and COX-2 gene expressions in RAW 264.7 macrophages. These .polyphenolic compounds are flavonoids. The effects of baicalin, baicalein and wogonin on LPS-induced NO production in RAW 264.7 macrophages were investigated by measuring the accumulated nitrite, estimated by the Griess reaction, in the culture medium. Unstimulated macrophages, after 24 hours of incubation in the culture medium, produced background levels of nitrite. When the cells were incubated with each of the three compounds alone, the concentration of nitrite in the medium was maintained at a background level similar to that in the unstimulated samples. After treatment with LPS (100 ng/mL) for 24 hours, nitrite concentrations in the medium increased remarkably by about 20 fold (~30 μM). When RAW 264.7 macrophages were treated with different concentrations of each of the three compounds together with LPS (100 μg/mL) for 24 hours, significant concentration-dependent inhibition of nitrite production was detected in the presence of baicalin, baicalein and wogonin. The $IC_{50}$ values of baicalin, baicalein and wogonin in inhibiting LPS-induced NO production were 15±1.4, 19.4±1.0 and 9.5±0.8 μM (n=3), respectively. Accordingly, the rank of potencies in inhibiting LPS-induced NO production was wogonin>baicalin>baicalein (p<0.01, n=3). Examination of cytotoxicity of baicalin, baicalein and wogonin in RAW 264.7 macrophages by MTT assay indicated that all three compounds, even at 40 μM, did not affect viability of RAW 264.7 cells. Therefore, inhibition of LPS-induced nitrite production by baicalin, baicalein and wogonin was not due to possible cytotoxic effect on these cells. The results indicated that these three polyphenolic compounds like oroxylin A inhibited LPS-induced NO production in a concentration-dependent manner without notable cytotoxic effect on these cells.

Decrease in NO production was in parallel with the inhibition by these polyphenolic compounds of LPS-induced iNOS gene expression. RAW 264.7 cells did not express detectable iNOS protein when incubated in the medium without LPS for 24 hours, and the basal level of iNOS protein was not affected when incubated with baicalin, baicalein or wogonin alone. Upon LPS (100 ng/mL) treatment for 24 hours, iNOS protein drastically increased in these cells, and co-treatment of cells with LPS (100 ng/mL) and different concentrations (20, 40 μM) of each of the three compounds for 24 hours significantly inhibited iNOS protein induction in RAW 264.7 macrophages. The amount of α-tubulin protein as an internal control remained unchanged.

Un-stimulated RAW 264.7 macrophages in culture medium for 24 hours produced basal amount of $PGE_2$ (1.5 ng/mL) in the medium. After treatment with LPS (100 ng/mL) for 24 hours, the medium concentration of PGE2 elevated significantly to 7 ng/mL. This increase was inhibited by co-treatment of cells with different concentrations of wogonin (20 and 40 μM). However, LPS-induced PGE2 production was not inhibited by baicalin or baicalein except at 40 μM, the highest concentration examined. Western blot analysis demonstrated that unstimulated RAW 264.7 macrophages expressed only a small amount of COX-2 proteins. Baicalin, baicalein, and wogonin treatment alone did not affect the basal COX-2 expression. Upon LPS (100 ng/mL) treatment for 24 hours, COX-2 protein drastically increased in these cells. The increase was significantly inhibited by co-treatment of cells with different concentrations (20, 40 μM) of wogonin for 24 hours. Baicalin and baicalein at similar concentrations did not inhibit LPS-induced COX-2 protein synthesis.

Wogonin, baicalein and baicalin, however, did not directly affect iNOS or COX-2 enzyme activity. Table 2 indicates that the addition of different concentrations (20 or 40 μM) of baicalin, baicalein, and wogonin to RAW 264.7 macrophages, which had been pre-treated with LPS to induce iNOS, did not affect iNOS enzyme activity in intact cells by measuring the amount of nitrite production in the medium. In parallel experiments, NOS inhibitors N-nitro-L-arginine (NLA) and N-nitro-L-arginine methyl ester (L-NAME) significantly decreased the nitrite production in the medium, but did not alter the iNOS enzyme activity in the cell lysates by direct NOS enzyme activity assays in vitro. Lack of direct enzyme inhibition by baicalin, baiclein and wogonin was further supported by findings that different concentrations (20, 40 μM) of baicalin, baicalein, and wogonin did not inhibit LPS-induced NO production, while it was significantly inhibited by both NLA and L-NAME treatment (Table 3).

When different concentrations (20 or 40 μM) of baicalin, baicalein and wogonin were added to RAW 264.7 macrophages in which COX-2 proteins had already been induced by LPS, there was no decrease in $PGE_2$ production using added arachidonic acid as a substrate (Table 4). Both NLA and L-NAME did not affect $PGE_2$ production, which however was significantly inhibited by indomethacin, a cyclooxygenase enzyme inhibitor.

It has been suggested that NO is a key factor in terminating the inflammation through an autoregulatory feedback inhibition of iNOS synthesis in LPS or cytokines treated cells. Accordingly, NOS enzyme inhibitors such as NLA and L-NAME significantly inhibit NO production, while these inhibitors stimulate iNOS gene expression. In the present study, NLA and L-NAME significantly inhibited LPS-induced NO (but not $PGE_2$) production (Table 5). NLA and L-NAME enhanced LPS (100 ng/mL)-induced iNOS (but not COX-2) gene expression by about 3-fold (**P<0.01, compared with LPS-treated group) by western blot analysis. The increased expression of iNOS was inhibited by baicalin, baicalein or wogonin in a concentration-dependent manner. Wogonin but not baicalin or baicalein inhibited expression of COX-2 proteins in NLA (or L-NAME) plus LPS co-treated RAW 264.7 macrophages. These results indicated that co-treatment with NOS inhibitors and polyphenolic compounds such as wogonin effectively blocked acute production of NO and, at the same time, inhibited expressions of iNOS and COX-2 genes. Wogonin like oroxylin A in combination with NOS inhibitors appears to be useful in the prevention and treatment of diseases due to increased expression of iNOS and COX-2 such as in endotoxemia.

TABLE 2

Effects of baicalin, baicalein and wongonin on LPS-induced NO synthesis and iNOS enzyme activity in RAW 264.7 macrophages.

| LPS pretreatment of cells | Addition to LPS-treated RAW 264.7 cells | NO in medium ($\mu$M/6 × 10$^5$ cells) | iNOS specific activity: NO formation ($\mu$M/200 $\mu$g protein) |
|---|---|---|---|
| None | DMSO control | 0.0 ± 0.0 | 1.5 ± 0.8 |
| LPS (100 ng/ml), 12 hours | Control | 16.9 ± 0.5 | 8.9 ± 1.2 |
| | Baicalein | | |
| | 20 $\mu$M | 15.4 ± 0.3 | 9.8 ± 2.3 |
| | 40 $\mu$M | 13.1 ± 0.9 | 8.1 ± 1.9 |
| | Baicalin | | |
| | 20 $\mu$M | 14.5 ± 0.5 | 8.7 ± 1.3 |
| | 40 $\mu$M | 14.8 ± 1.5 | 9.4 ± 2.1 |
| | Wogonin | | |
| | 20 $\mu$M | 16.5 ± 0.3 | 8.7 ± 3.1 |
| | 40 $\mu$M | 16.3 ± 0.3 | 8.9 ± 2.7 |
| | NLA | | |
| | 2 mM | 0.3 ± 0.1** | 9.4 ± 2.1 |
| | L-NAME | | |
| | 2 mM | 0.4 ± 0.2** | 9.7 ± 1.5 |

RAW264.7 macrophages were stimulated with LPS (100 ng/mL) for 12 hours and cells were washed twice with PBS to remove LPS. RAW cells were then scraped and placed in a 24-well plate and the indicated compounds were added and incubated at 37° C. incubator for additional 12 hours. The amount of NO accumulated in the medium and alternation of iNOS enzyme activity in cell lysates were detected by indirect and direct NOS enzyme assays as described above. Data are mean ± SEM from three independent experiments.
**P < 0.01 indicates significantly different from LPS alone (unpaired t test).

TABLE 3

Effects of baicalin, baicalein, and wogonin on iNOS activity by direct enzyme activity assay in RAW 264.7 cell lysates.

| Pretreatment of cells before lysis | Addition to lysate | iNOS specific activity: NO formation ($\mu$M/200 $\mu$g total protein)$^a$ |
|---|---|---|
| None | DMSO | 1.1 ± 0.5 |
| LPS (100 ng/mL), 12 hr | DMSO | 8.6 ± 0.4 |
| | Baicalin | |
| | 20 $\mu$M | 8.7 ± 1.0 |
| | 40 $\mu$M | 9.0 ± 1.1 |
| | Baicalein | |
| | 20 $\mu$M | 7.2 ± 0.1 |
| | 40 $\mu$M | 9.2 ± 1.8 |
| | Wogonin | |
| | 20 $\mu$M | 8.1 ± 0.2 |
| | 40 $\mu$M | 7.5 ± 0.1 |
| | NLA | |
| | 4 mM | 4.2 ± 0.4** |
| | L-NAME | |
| | 4 mM | 3.9 ± 0.6** |

$^a$The values were obtained from three separate experiments and described as means ± SEM. Lysate preparation and iNOS activity assay were described above. Each indicated compound was added into lysates (200 $\mu$g) from LPS-treated RAW264.7 macrophages and iNOS activity was measured.
**P < 0.01 indicates significantly different from LPS alone (unpaired t test)

TABLE 4

Effects of added baicalein, baicalin, wogonin, indomethacin, NLA and L-NAME on LPS-induced COX-2 enzyme in RAW 264.7 cells

| LPS treatment of Cells$^a$ | Addition to LPS-treated RAW 264.7 cells | PGE2 (ng/mL)$^b$ |
|---|---|---|
| None | DMSO | 0.2 ± 0.0 |
| LPS | DMSO | 6.5 ± 0.2 |
| | Baicalin | |
| | 20 $\mu$M | 6.1 ± 0.6 |
| | 40 $\mu$M | 5.9 ± 0.4 |
| | Baicalein | |
| | 20 $\mu$M | 6.1 ± 0.2 |
| | 40 $\mu$M | 6.2 ± 0.5 |
| | Wogonin | |
| | 20 $\mu$M | 5.9 ± 0.7 |
| | 40 $\mu$M | 5.7 ± 0.4 |
| | Indomethacin | |
| | 20 $\mu$M | 2.0 ± 0.7** |
| | NLA | |
| | 2 mM | 5.6± 0.9 |
| | L-NAME | |
| | 2 mM | 6.2 ± 0.6 |

$^a$RAW264.7 cells were stimulated with LPS (100 ng/mL) for 6 hours, and cells were washed twice with fresh medium. Baicalin, baicalein or other indicated compounds was then added and incubated at 37° C. for 30 min. The cells were further incubated with arachidonic acid (100 $\mu$M) for 15 min.
$^b$The amount of PGE2 in the supernatant was assayed as described above. Data are means ± SEM of three samples from two independent experiments. In each experiment, duplicate determinations were made for each experiment.
**P < 0.01 indicates significantly different from LPS alone (unpaired t test)

TABLE 5

Effects of baicalin, baicalein; wogonin on NLA or L-NAME stimulated LPS-induced NO and PGE2 productions in RAW 264.7 macrophages$^a$.

| Treatment of cells | NO ($\mu$mole/4 × 10$^5$) | PGE2 (ng/mL) |
|---|---|---|
| Control | 3.7 ± 0.7 | 1.8 ± 0.4 |
| LPS | 30.0 ± 0.6 | 7.1 ± 0.8 |
| NLA (2 mM)) | 3.7 ± 0.3 | 1.5 ± 0.5 |
| LPS + NLA (2 mM) | 9.7 ± 0.2** | 7.2 ± 0.6 |
| LPS + NLA (2 mM) + Baicalin (40 $\mu$M) | 7.1 ± 0.3** | 5.8 ± 1.1 |
| LPS + NLA (2 mM) + Baicalein (40 $\mu$M) | 8.3 ± 1.3** | 5.5 ± 0.8* |
| LPS + NLA (2 mM) + Wogonin (40 $\mu$M) | 6.7 ± 0.7** | 2.1 ± 0.4** |
| L-NAME (2 mM) | 5.1 ± 0.4 | 1.3 ± 0.6 |
| LPS + L-NAME (2 mM) | 7.3 ± 1.2** | 6.9 ± 0.9 |
| LPS + L-NAME (2 mM) + Baicalin (40 $\mu$M) | 8.5 ± 0.9** | 6.1 ± 0.3 |
| LPS + L-NAME (2 mM) + Baicalein (40 $\mu$M) | 7.9 ± 1.2** | 6.2 ± 0.5 |
| LPS + L-NAME (2 mM) + Wogonin (40 $\mu$M) | 6.8 ± 0.5** | 2.3 ± 0.7** |

$^a$RAW 264.7 cells were co-treated with LPS (100 ng/mL) and indicated compounds for 24 hours.
The amount of NO and PGE2 accumulated in the supernatant was detected by Griess assay and PGE2 assay kit as described above.
Data are means ± SE from three independent experiments.
*P < 0.05 and **P < 0.01 indicate significant difference from LPS alone (unpaired t test).

All references cited are hereby incorporated by reference. The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

---

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:1:

AGTTGAGGGG ACTTTCCCAG GC      22

(2) INFORMATION FOR SEQ ID NO:2:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:2:

AGTTGAGGCG ACTTTCCCAG GC      22

---

Changes can be made in the composition, operation and arrangement of the method of the present invention described herein without departing from the concept and scope of the invention as defined in the following claims:

We claim:

1. A method for inhibiting expression of inducible nitric oxide synthase comprising administering to a mammal in need thereof an effective nitric oxide synthase-inhibiting amount of a flavone and pharmaceutically acceptable salts thereof.

2. The method of claim 1 wherein said flavone is of the structure

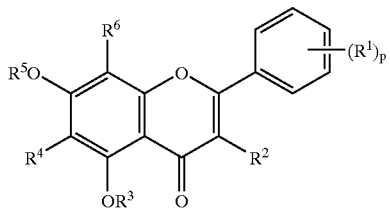

wherein p is an integer of zero to five;

$R^1$, at each occurrence, is independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-CO($C_1$–$C_3$ alkyl), $C_1$–$C_3$ alkylamino, alkenylamino, alkynylamino, di($C_1$–$C_3$ alkyl)amino, COOH, heterocyclylalkyl, C(O)O—($C_1$–$C_3$ alkyl), C(O)NH—($C_1$–$C_3$ alkyl), C(O)N($C_1$–$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

$R^2$, $R^4$ and $R^6$ are each independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-C(O)($C_1$–$C_3$ alkyl), $C_1$–$C_3$ alkylamino, alkenylamino, alkynylamino, di($C_1$–$C_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, and aryloxyalkyl; and $R^3$ and $R^5$ are each independently selected from the group consisting of hydrogen, $C_1$–$C_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;

wherein $R^1$, $R^2$, $R^3$, $R^4$, $R^5$ and $R^6$ are unsubstituted or substituted with at least one electron donating or electron withdrawing group.

3. The method of claim 2 wherein p is zero, $R^2$, $R^3$, $R^5$ and $R^6$ are hydrogen, and $R^4$ is methoxy.

4. The method of claim 2 wherein p is zero, $R^2$, $R^3$, $R^4$ and $R^5$ are hydrogen, and $R^6$ is methoxy.

5. The method of claim 1 further comprising the step of administering to the mammal a bactericidal amount of an antibiotic.

6. A method for inhibiting expression of cyclooxygenase-2 comprising administering to a mammal in need thereof an effective cyclooxygenase-2-inhibiting amount of a flavone and pharmaceutically acceptable salts thereof.

7. The method of claim 6 wherein said flavone is of the structure

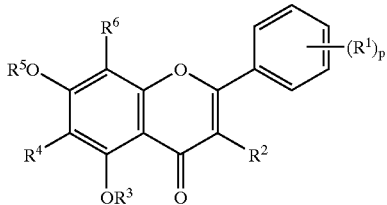

wherein p is an integer of zero to five;
R$^1$, at each occurrence, is independently selected from the group consisting of hydrogen, halogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-CO(C$_1$–C$_3$ alkyl), C$_1$–C$_3$ alkylamino, alkenylamino, alkynylamino, di(C$_1$–C$_3$ alkyl)amino, COOH, heterocyclylalkyl, C(O)O—(C$_1$–C$_3$ alkyl), C(O)NH—(C$_1$–C$_3$ alkyl), C(O)N(C$_1$–C$_3$alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, carbamate, aryloxyalkyl and C(O)NH(benzyl);
R$^2$, R$^4$ and R$^6$ are each independently selected from the group consisting of hydrogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-C(O)(C$_1$–C$_3$ alkyl), C$_1$–C$_3$ alkylamino, alkenylamino, alkynylamino, di(C$_1$–C$_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, halogen, and aryloxyalkyl; and
R$^3$ and R$^5$ are each independently selected from the group consisting of hydrogen, C$_1$–C$_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;
wherein R$^1$, R$^2$, R$^3$, R$^4$, R$^5$ and R$^6$ are unsubstituted or substituted with at least one electron donating or electron withdrawing group.

8. The method of claim 7 wherein p is zero, R$^2$, R$^3$, R$^5$ and R$^6$ are hydrogen, and R$^4$ is methoxy.

9. The method of claim 7 wherein p is zero, R$^2$, R$^3$, R$^4$ and R$^5$ are hydrogen, and R$^6$ is methoxy.

10. The method of claim 6 further comprising the step of administering to the mammal a bactericidal amount of an antibiotic.

11. A method for inhibiting expression of cyclooxygenase-2 and inducible nitric oxide synthase comprising administering to a mammal in need thereof an effective cyclooxygenase-2-and-nitric oxide synthase-inhibiting amount of a flavone and pharmaceutically acceptable salts thereof.

12. The method of claim 11 wherein said flavone is of the structure

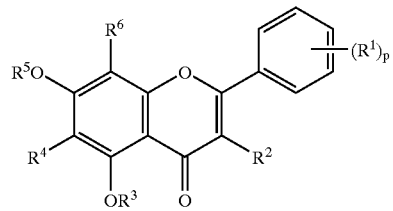

wherein p is an integer of zero to five;
R$^1$, at each occurrence, is independently selected from the group consisting of hydrogen, halogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-CO(C$_1$–C$_3$ alkyl), C$_1$–C$_3$ alkylamino, alkenylamino, alkynylamino, di(C$_1$–C$_3$ alkyl)amino, COOH, heterocyclylalkyl, C(O)O—(C$_1$–C$_3$ alkyl), C(O)NH—(C$_1$–C$_3$ alkyl), C(O)N(C$_1$–C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);
R$^2$, R$^4$ and R$^6$ are each independently selected from the group consisting of hydrogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-C(O)(C$_1$–C$_3$ alkyl), C$_1$–C$_3$ alkylamino, alkenylamino, alkynylamino, di(C$_1$–C$_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, amino, halogen, hydroxyl and aryloxyalkyl; and
R$^3$ and R$^5$ are each independently selected from the group consisting of hydrogen, C$_1$–C$_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;
wherein R$^1$, R$^2$, R$^3$, R$^4$, R$^5$ and R$^6$ are unsubstituted or substituted with at least one electron donating or electron withdrawing group.

13. The method of claim 12 wherein p is zero, R$^2$, R$^3$, R$^5$ and R$^6$ are hydrogen, and R$^4$ is methoxy.

14. The method of claim 12 wherein p is zero, R$^2$, R$^3$, R$^4$ and R$^5$ are hydrogen, and R$^6$ is methoxy.

15. The method of claim 11 further comprising the step of administering to the mammal a bactericidal amount of an antibiotic.

16. A method for activating potassium channels comprising administering to a mammal in need thereof an effective potassium channel activating amount of a flavone and pharmaceutically acceptable salts thereof.

17. The method of claim 16 wherein said flavone is of the structure

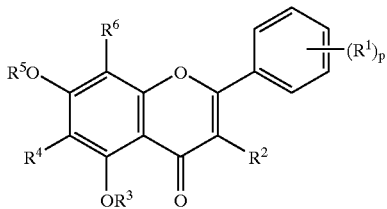

wherein p is an integer of zero to five;

R$_1$, at each occurrence, is independently selected from the group consisting of hydrogen, halogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-CO(C$_1$–C$_3$ alkyl), C$_1$–C$_3$ alkylamino, alkenylamino, alkynylamino, di(C$_1$–C$_3$ alkyl)amino, COOH, heterocyclylalkyl, C(O)O—(C$_1$–C$_3$ alkyl), C(O)NH—(C$_1$–C$_3$ alkyl), C(O)N(C$_1$–C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

R$^2$, R$^4$ and R$^6$ are each independently selected from the group consisting of hydrogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-C(O)(C$_1$–C$_3$ alkyl), C$_1$–C$_3$ alkylamino, alkenylamino, alkynylamino, di(C$_1$–C$_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, halogen, hydroxyl and aryloxyalkyl; and R$^3$ and R$^5$ are each independently selected from the group consisting of hydrogen, C$_1$–C$_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;

wherein R$^1$, R$^2$, R$^3$, R$^4$, R$^5$ and R$^6$ are unsubstituted or substituted with at least one electron donating or electron withdrawing group.

18. The method of claim 17 wherein p is zero, R$^2$, R$^3$, R$^5$ and R$^6$ are hydrogen, and R$^4$ is methoxy.

19. The method of claim 17 wherein p is zero, R$^2$, R$^3$, R$^4$ and R$^5$ are hydrogen, and R$^6$ is methoxy.

20. The method of claim 16 further comprising the step of administering to the mammal a bactericidal amount of an antibiotic.

21. A method for treating septic shock comprising administering to a mammal in need thereof a therapeutically effective amount of a flavone having one alkoxy group and pharmaceutically acceptable salts thereof.

22. The method of claim 21 wherein said flavone is of the structure

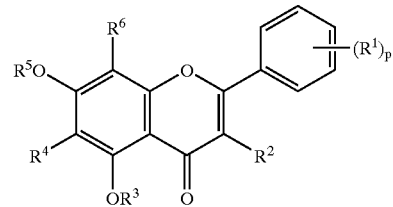

wherein p is an integer of zero to five;

R$^1$, at each occurrence, is independently selected from the group consisting of hydrogen, halogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, CN, NO$_2$, OH, NH$_2$, CH=NOH, SO$_2$—(C$_1$–C$_3$ alkyl), SO$_3$—(C$_1$–C$_3$ alkyl), N(C$_1$–C$_3$ alkyl)-CO(C$_1$–C$_3$ alkyl), C$_1$–C$_3$ alkylamino, alkenylamino, alkynylamino, di(C$_1$–C$_3$ alkyl)amino, COOH, heterocyclylalkyl, C(O)O—(C$_1$–C$_3$ alkyl), C(O)NH—(C$_1$–C$_3$ alkyl), C(O)N(C$_1$–C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

R$^2$, R$^4$ and R$^6$ are each independently selected from the group consisting of hydrogen, C$_1$–C$_6$ alkyl, C$_1$–C$_6$ alkenyl, C$_1$–C$_6$ alkynyl, C$_1$–C$_6$ alkoxy, alkenoxy, alkynoxy, thioalkoxy, aliphatic acyl, CF$_3$, nitro, cyano, N(C$_1$–C$_3$ alkyl)-C(O)(C$_1$–C$_3$ alkyl), C$_1$–C$_3$ alkylamino, alkenylamino, alkynylamino, di(C$_1$–C$_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, amino, hydroxyl, halogen and aryloxyalkyl; and R$^3$ and R$^5$ are each independently selected from the group consisting of hydrogen, C$_1$–C$_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;

wherein R$^1$, R$^2$, R$^3$, R$^4$, R$^5$ and R$^6$ are unsubstituted or substituted with at least one electron donating or electron withdrawing group, provided that only one of R$^1$, R$^2$, R$^3$, R$^4$, R$^5$ and R$^6$ may be alkoxy.

23. The method of claim 22 wherein p is zero, R$^2$, R$^3$, R$^5$ and R$^6$ are hydrogen, and R$^4$ is methoxy.

24. The method of claim 22 wherein p is zero, R$^2$, R$^3$, R$^4$ and R$^5$ are hydrogen, and R$^6$ is methoxy.

25. The method of claim 21 further comprising the step of administering to the mammal a bactericidal amount of an antibiotic.

26. A method for reducing inflammation comprising administering to a mammal in need thereof an inflammation-reducing amount of a flavone and pharmaceutically acceptable salts thereof.

27. The method of claim 26 wherein said flavone is of the structure

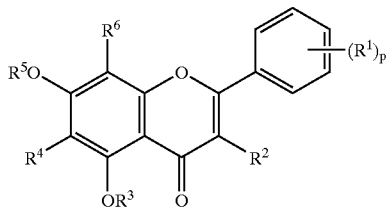

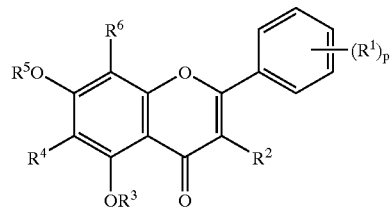

wherein p is an integer of zero to five;

R$^1$, at each occurrence, is independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), $N(C_1$–$C_3$ alkyl)-CO($C_1$–$C_3$ alkyl), $C_1$–$C_3$ alkylamino, alkenylamino, alkynylamino, di($C_1$–$C_3$ alkyl)amino, COOH, heterocyclylalkyl, C(O)O—($C_1$–$C_3$ alkyl), C(O)NH—($C_1$–$C_3$ alkyl), C(O)N($C_1$–$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

R$^2$, R$^4$ and R$^6$ are each independently selected from the group consisting of hydrogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), $N(C_1$–$C_3$ alkyl)-C(O)($C_1$–$C_3$ alkyl), $C_1$–$C_3$ alkylamino, alkenylamino, alkynylamino, di($C_1$–$C_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, halogen, and aryloxyalkyl; and R$^3$ and R$^5$ are each independently selected from the group consisting of hydrogen, $C_1$–$C_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;

wherein R$^1$, R$^2$, R$^3$, R$^4$, R$^5$ and R$^6$ are unsubstituted or substituted with at least one electron donating or electron withdrawing group.

28. The method of claim 27 wherein p is zero, R$^2$, R$^3$, R$^5$ and R$^6$ are hydrogen, and R$^4$ is methoxy.

29. The method of claim 27 wherein p is zero, R$^2$, R$^3$, R$^4$ and R$^5$ are hydrogen, and R$^6$ is methoxy.

30. The method of claim 26 further comprising the step of administering to the mammal a bactericidal amount of an antibiotic.

31. A method for inhibiting expression of angiotensin converting enzyme comprising administering to a mammal in need thereof an effective angiotensin converting enzyme-inhibiting amount of a flavone and pharmaceutically acceptable salts thereof.

32. The method of claim 31 wherein said flavone is of the structure wherein p is an integer of zero to five;

R$^1$, at each occurrence, is independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, $CF_3$, CN, $NO_2$, OH, $NH_2$, CH=NOH, $SO_2$—($C_1$–$C_3$ alkyl), $SO_3$—($C_1$–$C_3$ alkyl), $N(C_1$–$C_3$ alkyl)-CO($C_1$–$C_3$ alkyl), $C_1$–$C_3$ alkylamino, alkenylamino, alkynylamino, di($C_1$–$C_3$ alkyl)amino, COOH, heterocyclylalkyl, C(O)O—($C_1$–$C_3$ alkyl), C(O)NH—($C_1$–$C_3$ alkyl), C(O)N($C_1$–$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

R$^2$, R$^4$ and R$^6$ are each independently selected from the group consisting of hydrogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), $N(C_1$–$C_3$ alkyl)-C(O)($C_1$–$C_3$ alkyl), $C_1$–$C_3$ alkylamino, alkenylamino, alkynylamino, di($C_1$–$C_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclylalkyl, sulfonamido, halogen, and aryloxyalkyl; and R$^3$ and R$^5$ are each independently selected from the group consisting of hydrogen, $C_1$–$C_6$ alkyl, alkenyl, alkynyl, aryl, aralkyl, biaryl, heterocyclyl, heterocycloyl, alkylheterocyclyl, heterocyclalkyl, cyanomethyl, cycloalkyl, cycloalkenyl and cycloalkylalkyl;

wherein R$^1$, R$^2$, R$^3$, R$^4$, R$^5$ and R$^6$ are unsubstituted or substituted with at least one electron donating or electron withdrawing group.

33. The method of claim 32 wherein p is zero, R$^2$, R$^3$, R$^5$ and R$^6$ are hydrogen, and R$^4$ is methoxy.

34. The method of claim 32 wherein p is zero, R$^2$, R$^3$, R$^4$ and R$^5$ are hydrogen, and R$^6$ is methoxy.

35. The method of claim 31 further comprising the step of administering to the mammal a bactericidal amount of an antibiotic.

36. A method for treating or preventing aneurysms comprising administering to a mammal in need thereof a pharmaceutically effective amount of a flavone or a pharmaceutically acceptable salt thereof.

37. The method of claim 36 wherein said flavone is of the structure

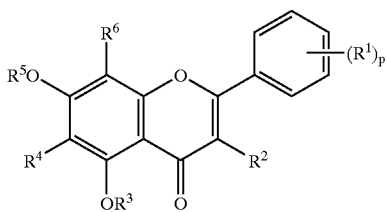

wherein p is an integer of zero to five;

R¹, at each occurrence, is independently selected from the group consisting of hydrogen, halogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-CO ($C_1$–$C_3$ alkyl), $C_1$–$C_3$ alkylamino, alkenylamino, alkynylamino, di($C_1$–$C_3$ alkyl)amino, COOH, heterocyclylalkyl, C(O)O—($C_1$–$C_3$ alkyl), C(O)NH—($C_1$–$C_3$ alkyl), C(O)N($C_1$–$C_3$alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, alkylheterocyclyl, sulfonamido, carbamate, aryloxyalkyl and C(O)NH(benzyl);

$R^2$, $R^4$ and $R^6$ are each independently selected from the group consisting of hydrogen, $C_1$–$C_6$ alkyl, $C_1$–$C_6$ alkenyl, $C_1$–$C_6$ alkynyl, $C_1$–$C_6$ alkoxy, alkenoxy, alkynoxy, thioalkoxy, aliphatic acyl, $CF_3$, CN, $NO_2$, OH, $NH_2$, CH=NOH, $SO_2$—($C_1$–$C_3$ alkyl), $SO_3$—($C_1$–$C_3$ alkyl), N($C_1$–$C_3$ alkyl)-C(O)($C_1$–$C_3$ alkyl), $C_1$–$C_3$ alkylamino, alkenylamino, alkynylamino, di($C_1$–$C_3$ alkyl)amino, haloalkyl, alkoxylcarbonyl, alkoxyalkoxy, cycloalkyl, cycloalkenyl, cycloalkynyl, aryl, aroyl, aryloxy, arylamino, biaryl, thioaryl, alkylaryl, aralkyl, sulfonyl, heterocyclyl, heterocycloyl, alkylheterocyclyl, heterocyclalkyl, sulfonamido, halogen, and aryloxyalkyl; and $R^3$ and $R^5$ are each independently selected from the group consisting of hydrogen, $C_1$–$C_6$ alkyl, alkenyl, alkynyl, aryl, aralkyl, biaryl, heterocyclyl, heterocycloyl, alkylheterocyclyl, heterocyclylalkyl, cyanomethyl, cycloalkyl, cycloalkenyl and cycloalkylalkyl;

wherein $R^1$, $R^2$, $R^3$, $R^4$, $R^5$ and $R^6$ are unsubstituted or substituted with at least one electron donating or electron withdrawing group.

38. The method of claim 37 wherein p is zero, $R^2$, $R^3$, $R^5$ and $R^6$ are hydrogen, and $R^4$ is methoxy.

39. The method of claim 37 wherein p is zero, $R^2$, $R^3$, $R^4$ and $R^5$ are hydrogen, and $R^6$ is methoxy.

40. The method of claim 36 further comprising the step of administering to the mammal a bactericidal amount of an antibiotic.

41. A method of treating septic shock in a patient comprising:
(a) giving the patient an effective amount of an inhibitor of the iNOS enzyme;
(b) giving the patient an effective amount of an inhibitor of the synthesis of at least one of the iNOS enzyme and the COX-2 enzyme; and
(c) maintaining suppression of the iNOS or COX-2 enzyme until the cause of the septic shock is removed or overcome.

42. The method of claim 41 wherein step (b) comprises inhibiting the synthesis of both the COX-2 and iNOS enzymes.

43. The method of claim 42 where the compound inhibiting the synthesis of the COX-2 and iNOS enzymes is a non-polymethoxylated flavone or salt thereof.

44. The method of claim 42 wherein the compound inhibiting the synthesis of the COX-2 and iNOS enzymes has no methoxy groups or a single methoxy group.

45. The method of claim 44 wherein the compound is oroxylin A or wogonin.

46. A method of treating chronic inflammation comprising
(a) giving the patient an effective amount of an inhibitor of the COX-2 enzyme;
(b) giving the patient an effective amount of an inhibitor of the synthesis of the synthesis of the iNOS enzyme and/or the COX-2 enzyme; and
(c) maintaining suppression of the iNOS enzyme or COX-2 enzyme until the cause of the chronic inflammation is removed or overcome.

47. The method of claim 46 wherein step (b) comprises inhibiting the synthesis of both the COX-2 and iNOS enzymes.

48. The method of claim 47 where the compound inhibiting the synthesis of the COX-2 and iNOS enzymes is a non-polymethoxylated flavone or salt thereof.

49. The method of claim 48 wherein the compound inhibiting synthesis of the COX 2 and iNOS enzymes has no methoxy groups or a single methoxy group.

50. The method of claim 49 wherein the compound is oroxylin A or wogonin.

* * * * *